(12) United States Patent
Matityahu

(10) Patent No.: US 8,951,289 B2
(45) Date of Patent: Feb. 10, 2015

(54) SPINAL CONNECTION ASSEMBLY

(75) Inventor: Amir M. Matityahu, Los Altos, CA (US)

(73) Assignee: Total Connect Spine, LLC, Rancho Palos Verdes, CA (US)

( * ) Notice: Subject to any disclaimer, the term of this patent is extended or adjusted under 35 U.S.C. 154(b) by 290 days.

(21) Appl. No.: 12/575,396

(22) Filed: Oct. 7, 2009

(65) Prior Publication Data

US 2010/0094346 A1    Apr. 15, 2010

Related U.S. Application Data

(60) Provisional application No. 61/104,104, filed on Oct. 9, 2008.

(51) Int. Cl.
*A61B 17/70* (2006.01)
*A61B 17/86* (2006.01)

(52) U.S. Cl.
CPC ......... *A61B 17/863* (2013.01); *A61B 17/7038* (2013.01); *A61B 17/7041* (2013.01); *A61B 17/7044* (2013.01); *A61B 17/8605* (2013.01); *A61B 17/8635* (2013.01); *A61B 17/7049* (2013.01)
USPC ............................ 606/250; 606/278; 606/267

(58) Field of Classification Search
USPC ................ 606/246, 250–253, 260, 264–272, 606/276–278, 300, 301, 305–308
See application file for complete search history.

(56) References Cited

U.S. PATENT DOCUMENTS

| 4,653,489 A | 3/1987 | Tronzo |
| 4,790,303 A | 12/1988 | Steffee |
| 5,176,679 A | 1/1993 | Lin |
| 5,423,857 A * | 6/1995 | Rosenman et al. ........... 606/219 |
| 5,584,831 A * | 12/1996 | McKay ....................... 606/86 A |

(Continued)

FOREIGN PATENT DOCUMENTS

| FR | 2743290 | 7/1997 |
| WO | WO01/60270 | 8/2001 |

(Continued)

OTHER PUBLICATIONS

Dec. 4, 2009 International Search Report issued by the U.S. Patent and Trademark Office in the roll of ISA/US for corresponding PCT application serial No. PCT/US2009/059905, p. 1.

(Continued)

*Primary Examiner* — Ellen C Hammond
*Assistant Examiner* — Jacqueline Johanas
(74) *Attorney, Agent, or Firm* — Intellectual Innovations Legal Advisors

(57) ABSTRACT

A spinal connection assembly for use with a posterior spinal connector having a head and a groove adjacent the head for providing a neck and a connector element to treat a spine of a mammalian body is provided. The assembly includes a housing having first and second side portions and a top and a bottom. The first side portion is provided with a bottom-facing first opening adapted for receiving the posterior spinal connector. A capture mechanism is carried by the first side portion for engaging the head of the posterior spinal connector and extends at least partially into the groove so as to capture the head within the first opening. The second side portion is provided with a second opening. A securement mechanism is carried by the second side portion for capturing the connector element within the second opening.

25 Claims, 30 Drawing Sheets

(56) References Cited

U.S. PATENT DOCUMENTS

| | | | |
|---|---|---|---|
| 5,690,630 A | 11/1997 | Errico et al. | |
| 5,800,548 A * | 9/1998 | Martin et al. | 606/253 |
| 5,989,250 A | 11/1999 | Wagner et al. | |
| 6,063,089 A * | 5/2000 | Errico et al. | 606/278 |
| 6,083,226 A * | 7/2000 | Fiz | 606/252 |
| 6,171,311 B1 * | 1/2001 | Richelsoph | 606/252 |
| 6,280,443 B1 * | 8/2001 | Gu et al. | 606/264 |
| 6,325,805 B1 | 12/2001 | Ogilvie et al. | |
| 6,533,790 B1 | 3/2003 | Liu | |
| 6,749,614 B2 | 6/2004 | Teitelbaum et al. | |
| 6,755,830 B2 * | 6/2004 | Minfelde et al. | 606/278 |
| 6,866,664 B2 * | 3/2005 | Schär et al. | 606/252 |
| 6,887,241 B1 | 5/2005 | McBride et al. | |
| 6,923,811 B1 | 8/2005 | Carl et al. | |
| 7,572,276 B2 * | 8/2009 | Lim et al. | 606/246 |
| 7,585,314 B2 | 9/2009 | Taylor et al. | |
| 7,588,593 B2 * | 9/2009 | Aferzon | 606/265 |
| 7,604,655 B2 * | 10/2009 | Warnick | 606/265 |
| 7,625,396 B2 * | 12/2009 | Jackson | 606/305 |
| 7,666,210 B2 * | 2/2010 | Franck et al. | 606/250 |
| 7,744,632 B2 * | 6/2010 | Usher | 606/250 |
| 7,780,706 B2 * | 8/2010 | Marino et al. | 606/264 |
| 7,927,355 B2 * | 4/2011 | Berrevoets et al. | 606/250 |
| 7,938,829 B2 * | 5/2011 | Mullaney | 606/59 |
| 8,048,126 B2 * | 11/2011 | Altarac et al. | 606/267 |
| 8,197,515 B2 * | 6/2012 | Levy et al. | 606/250 |
| 8,308,782 B2 * | 11/2012 | Jackson | 606/308 |
| 8,337,530 B2 * | 12/2012 | Hestad et al. | 606/279 |
| 2002/0068975 A1 | 6/2002 | Teitelbaum et al. | |
| 2003/0028192 A1 | 2/2003 | Schar et al. | |
| 2003/0045879 A1 | 3/2003 | Minfelde et al. | |
| 2003/0171755 A1 | 9/2003 | Moseley et al. | |
| 2004/0087948 A1 * | 5/2004 | Suddaby | 606/61 |
| 2004/0186473 A1 | 9/2004 | Cournoyer et al. | |
| 2005/0080415 A1 | 4/2005 | Keyer et al. | |
| 2005/0080420 A1 * | 4/2005 | Farris et al. | 606/61 |
| 2005/0113831 A1 * | 5/2005 | Franck et al. | 606/61 |
| 2005/0197660 A1 | 9/2005 | Haid, Jr. et al. | |
| 2005/0228377 A1 * | 10/2005 | Chao et al. | 606/61 |
| 2005/0228382 A1 | 10/2005 | Richelsoph et al. | |
| 2005/0240266 A1 | 10/2005 | Kuiper et al. | |
| 2005/0246023 A1 | 11/2005 | Yeung | |
| 2005/0261770 A1 | 11/2005 | Kuiper et al. | |
| 2005/0267481 A1 | 12/2005 | Carl et al. | |
| 2006/0058789 A1 * | 3/2006 | Kim et al. | 606/61 |
| 2006/0084982 A1 | 4/2006 | Kim | |
| 2006/0111715 A1 * | 5/2006 | Jackson | 606/61 |
| 2006/0149244 A1 * | 7/2006 | Amrein et al. | 606/61 |
| 2006/0195094 A1 | 8/2006 | McGraw et al. | |
| 2006/0200151 A1 | 9/2006 | Ducharme et al. | |
| 2006/0235389 A1 | 10/2006 | Albert et al. | |
| 2006/0235414 A1 | 10/2006 | Lim et al. | |
| 2006/0247626 A1 * | 11/2006 | Taylor et al. | 606/61 |
| 2006/0271045 A1 * | 11/2006 | Hubbard et al. | 606/61 |
| 2006/0271054 A1 | 11/2006 | Sucec et al. | |
| 2006/0282074 A1 * | 12/2006 | Renaud et al. | 606/61 |
| 2007/0043355 A1 * | 2/2007 | Bette et al. | 606/61 |
| 2007/0118123 A1 * | 5/2007 | Strausbaugh et al. | 606/61 |
| 2007/0270817 A1 * | 11/2007 | Rezach | 606/61 |
| 2008/0015579 A1 * | 1/2008 | Whipple | 606/61 |
| 2008/0015597 A1 * | 1/2008 | Whipple | 606/73 |
| 2008/0058809 A1 * | 3/2008 | Graf | 606/61 |
| 2008/0172093 A1 * | 7/2008 | Nilsson | 606/250 |
| 2008/0177315 A1 * | 7/2008 | Usher | 606/253 |
| 2008/0177317 A1 | 7/2008 | Jackson | |
| 2008/0312655 A1 * | 12/2008 | Kirschman et al. | 606/60 |
| 2009/0005813 A1 * | 1/2009 | Crall et al. | 606/246 |
| 2009/0018586 A1 * | 1/2009 | Butler et al. | 606/278 |
| 2009/0036928 A1 * | 2/2009 | Kim et al. | 606/278 |
| 2009/0036929 A1 * | 2/2009 | Reglos et al. | 606/278 |
| 2009/0143823 A1 * | 6/2009 | Jeon et al. | 606/250 |
| 2009/0177234 A1 * | 7/2009 | Butler et al. | 606/277 |
| 2009/0287253 A1 * | 11/2009 | Felix et al. | 606/278 |
| 2010/0016903 A1 | 1/2010 | Matityahu et al. | |
| 2010/0094346 A1 | 4/2010 | Matityahu | |
| 2010/0204735 A1 * | 8/2010 | Gephart et al. | 606/264 |
| 2010/0234893 A1 * | 9/2010 | Iott et al. | 606/278 |
| 2010/0241168 A1 * | 9/2010 | Franck et al. | 606/250 |
| 2010/0241172 A1 * | 9/2010 | Biyani et al. | 606/279 |
| 2010/0268279 A1 * | 10/2010 | Gabelberger et al. | 606/278 |
| 2010/0305612 A1 * | 12/2010 | Nilsson | 606/250 |
| 2012/0123486 A1 * | 5/2012 | Werner et al. | 606/308 |
| 2013/0144346 A1 * | 6/2013 | Jackson et al. | 606/305 |

FOREIGN PATENT DOCUMENTS

| | | |
|---|---|---|
| WO | WO 2007/053960 | 11/2005 |
| WO | WO2007/041648 | 4/2007 |
| WO | WO2008/014477 | 1/2008 |
| WO | WO2008/021319 | 2/2008 |

OTHER PUBLICATIONS

Dec. 4, 2009 Written Opinion of the International Searching Authority issued by the U.S. Patent and Trademark Office in the roll of ISA/US for corresponding PCT application serial No. PCT/US2009/059905, pp. 1-6.

Jun. 17, 2009 International Search Report issued by the U.S. Patent and Trademark Office in the roll of ISA/US for corresponding PCT application serial No. PCT/US2009/041160, p. 1.

Oct. 26, 2010 International Preliminary Report on Patentability issued by the U.S. Patent and Trademark Office in the roll of ISA/US for corresponding PCT application serial No. PCT/US2009/041160, pp. 1-7.

Feb. 28, 2012 Official Action cited by Chinese Patent Office with English Translation, related Chinese Patent Application No. 200980120156.0, McKesson Reference, pp. 1-8.

Aug. 27, 2012 Instructions for response to Feb. 28, 2012 Chinese Official Action, related Chinese Patent Application No. 200980120156.0, McKesson Reference, pp. 1-11.

Aug. 4, 2011 Restriction Requirement issued by the U.S. Patent Office, related U.S. Appl. No. 12/426,898, McKesson Reference, pp. 1-7.

Response to Aug. 4, 2011 Restriction Requirement filed on Sep. 28, 2011, related U.S. Appl. No. 12/426,898, McKesson Reference, pp. 1-9.

Nov. 10, 2011 Non-Final Office Action issued by the U.S. Patent Office, related U.S. Appl. No. 12/426,898, McKesson Reference, pp. 1-8.

Response to Nov. 10, 2011 Non-Final Office Action filed on May 10, 2012, related U.S. Appl. No. 12/426,898, McKesson Reference, pp. 1-8.

Jul. 27, 2012 Final Office Action issued by the U.S. Patent Office, related U.S. Appl. No. 12/426,898, McKesson Reference, pp. 1-8.

Supplementary European Search Report issued by European Patent Office for copending EP patent application serial No. EP09734068, Dec. 19, 2012 pp. 1-5.

Response to Jul. 27, 2012 Final Office Action, Filed Response for U.S. Appl. No. 12/426,898 on Nov. 9, 2012, pp. 1-7.

Supplementary European Search Report issued by the European Patent Office for corresponding family matter, Serial No. EP09819848, Jul. 9, 2013 pp. 1-8.

Response mailed on Feb. 4, 2014 for European office action dated Jul. 26, 2013 for Application No. EP09819848.4 filed Oct. 7, 2009, 20 pages.

* cited by examiner

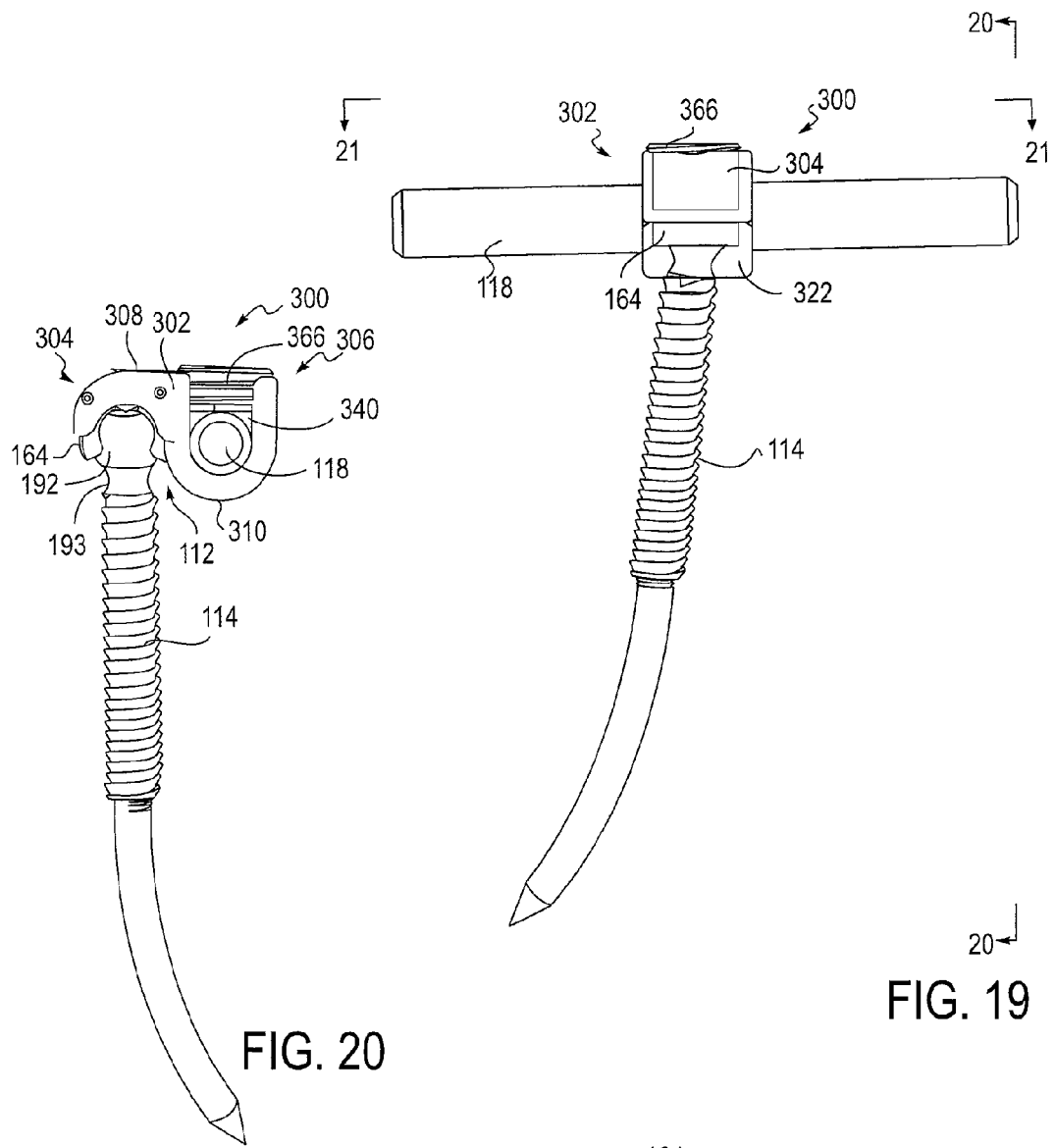
FIG. 20
FIG. 19
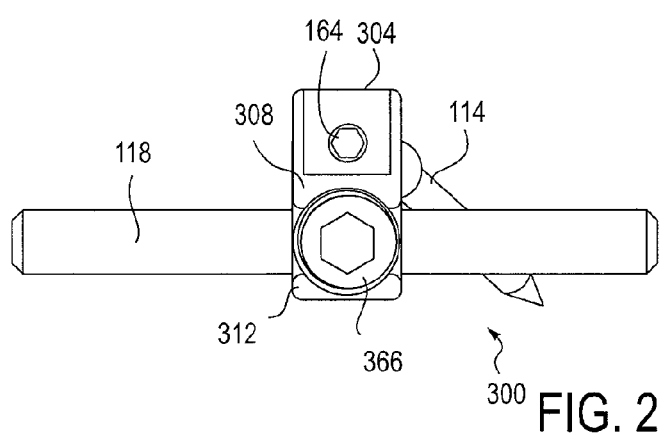
FIG. 21

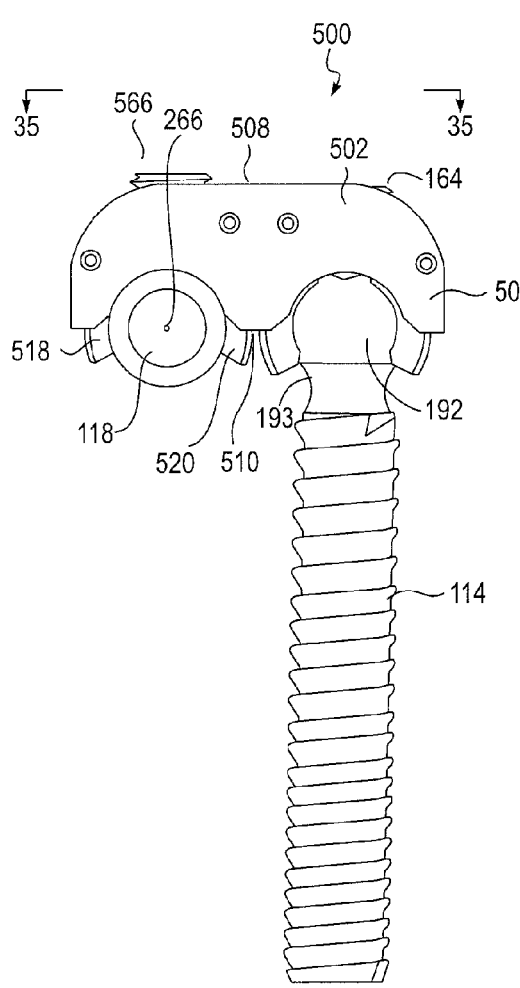
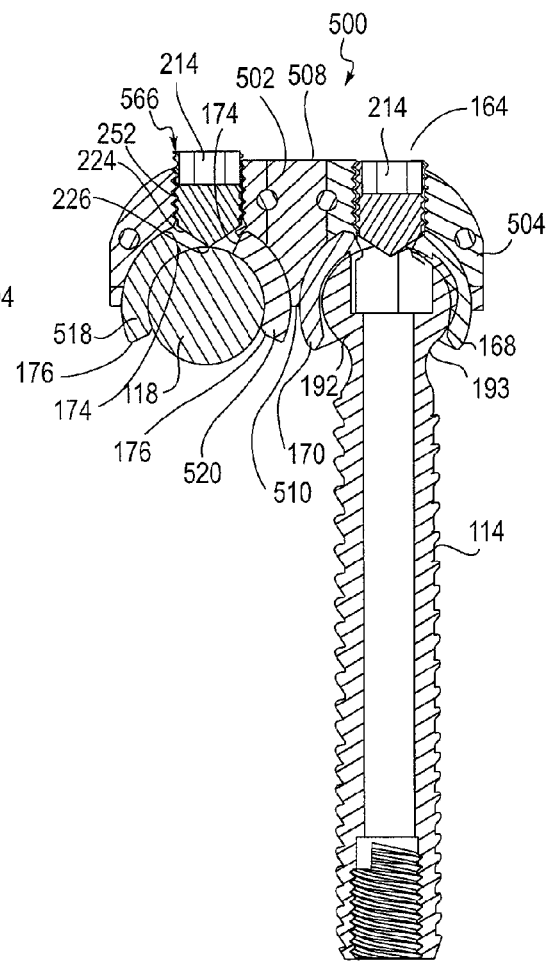
FIG. 33
FIG. 34

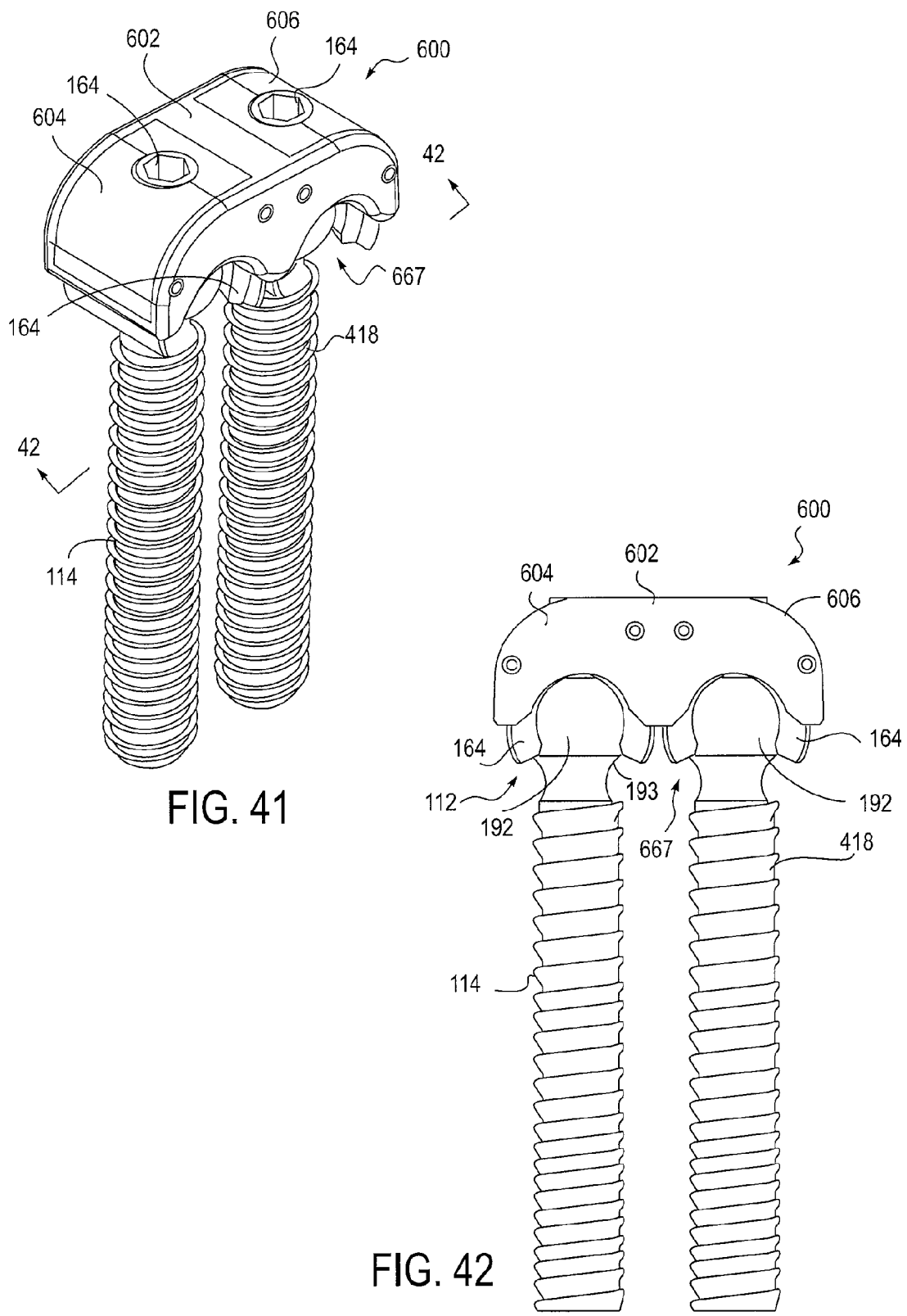

SPINAL CONNECTION ASSEMBLY

CROSS-REFERENCE TO RELATED APPLICATIONS

This application claims the benefit of related U.S. Provisional Patent Application Ser. No. 61/104,104 filed Oct. 9, 2008, the entire content of which is hereby incorporated by this reference.

SCOPE OF THE INVENTION

The present invention relates to medical implants and in particular to spinal connection assemblies.

BACKGROUND

As is known, spinal fusions can be utilized when there is a deformity of the spine, instability of the spine, a damaged intervertebral disk, trauma to the spine, a tumor on the spine, spinal pain or infection or degeneration of the spine. A number of posterior spinal fixation methods are available for stabilizing the spine and permitting fusion to occur. Commonly, these devices are adapted for use with posterior spinal screws that are inserted into the vertebrae.

A tulip is often provided on the posterior end of the posterior spinal screw for coupling the screw to a transverse rod that extends vertically along the spine. In this regard, the screw head is positioned within a recess formed at one end of a cylindrical-type tulip body. The rod sits in a recess at the other end of the cylindrical body. The recess is provided at the top end of the body and extends perpendicular to the longitudinal axis of the tulip so that the rod may extend perpendicular to the axis of the screw. A rod capturing screw may also be provided on the tulip. The vertical rod is coupled to one or more other screws, by means of tulips or otherwise, thus connecting several vertebral bodies together. Screws and rod serve as a mechanism to maintain the vertebral bodies in a generally fixed position relative to each other while they are fused together by a bone graft.

Other mechanisms exist for securing together posterior spinal screws. For example, a rigid single structure may be used. In one example of this embodiment, the a screw itself may have a recess extending transversely or perpendicular to the longitudinal axis of the screw, which recess is formed integral with the proximal or posterior end of the screw. The rod is seated in that recess, and is secured within the recess by a rod capturing screw or other suitable means. Other mechanisms include a side loading assembly. In one example of this embodiment, a securement mechanism sits over the posterior end of the screw and has a through-hole spaced from and perpendicular to the longitudinal axis of the screw. The rod is threaded through the securement mechanism. Alternatively, the rod may be threaded through a recess within the screw and which extends perpendicular to the screw, but is spaced or positioned along the longitudinal axis of the screw.

The rod may be pre-threaded through each of the various securement mechanisms. Once the screws are placed within the vertebrae, the securement mechanisms are placed over the respective screws. Alternatively, the securement mechanisms may be placed on the posterior end of the screws. Then the construct is placed within the recesses in the securement mechanisms.

Unfortunately, problems exist with each of the aforementioned systems. For instance, with respect to the tulip design, the rod sits posteriorly of the screw head. Thus, a pedicle or other posterior spinal screw having a tulip on top of it increases the distance between the pedicle screw head and the top of the mechanism that askews a rod, causing prominence of the total construct. Additionally, only a limited amount of rotation is permitted due to the geometry of currently used tulip devices. Namely the tulip can only rotate about a cone having a conical axis of thirty degrees from the central axis of the screw head. In order to load the rod into the tulip, or slot in the screw, if the rod is not directly in line with the slot, or on top of the tulip, or within the thirty degree cone of that tulip and the head of the screw, the physician must use a tool called a "persuader" in order to push or force the rod into the tulip. This causes preload on the pedicle screws within the pedicle. Moreover, a torquing of the pedicle may result as the physician forces the rod capturing screw on top of the tulip or screw, which then causes torsional stresses onto the pedicle screw. In order to avoid this, a physician must use a special tool that does not allow the torque to occur.

With respect to the side loading system, only one pivotal direction of the rod capturing mechanism exists for an embodiment having one opening. As a result, a physician must preload all the assemblies onto the rod first, and then where applicable, slide the preloaded assembly on to the screw that has already been placed in the body. In other words, a physician must preload the rod, and place the assemblies on the screw. Unfortunately, the physician must still persuade the rod into a side loading mechanism in order to make sure that it is exactly at the right level and in the anterior or posterior direction.

An additional disadvantage is that if a physician uses a facet screw or a laminopedicle screw, in which the screw is placed into the spine at a sharp angle, usually around forty-five to sixty degrees relative to the axis of the spine, or relative to the horizontal plane relative to the spine, tulips cannot be used. The cone of motion, or the polyaxiality of the tulip is only thirty degrees. Additionally, the tulip would be incredibly prominent if a facet screw or laminopedicle screw is used.

Accordingly, what is needed in the art is an improved system and device for stabilizing adjacent vertebra in the mammalian spine. More particularly, what is needed in the art is a low profile, non-prominent spinal connection assembly that allows motion of the spinal connection assembly relative to the head of the screw to which it is attached to be able to pivot in a large degree of motion in at least one plane, and preferably a large degree of motion in at least two planes, so as to be capable of pivoting about the axis of the screw head and thus decrease the pre-load and torque on the screw.

SUMMARY OF THE INVENTION

A low-profile side-by-side spinal connection assembly for use with a posterior spinal connector having a head and a groove adjacent the head for providing a neck and a connector element to treat a spine of a mammalian body is provided. The assembly includes a housing having first and second side portions and a top and a bottom. The first side portion is provided with a bottom-facing first opening adapted for receiving the posterior spinal connector. A capture mechanism is carried by the first side portion for engaging the head of the posterior spinal connector and extends at least partially into the groove so as to capture the head within the first opening. The second side portion is provided with a second opening. A securement mechanism is carried by the second side portion for capturing the connector element within the second opening.

BRIEF DESCRIPTION OF THE DRAWINGS

FIG. 19 is an elevational view of the spinal connection assembly of FIG. 18, taken from line 19-19 of FIG. 18.

FIG. 20 is an elevational view of the spinal connection assembly of FIG. 18, taken from line 20-20 of FIG. 19.

FIG. 21 is plan view of the spinal connection assembly of FIG. 18, taken from line 21-21 of FIG. 19.

FIG. 33 is an elevational view of the spinal connection assembly of FIG. 32, taken from line 33-33 of FIG. 32.

FIG. 34 is a cross-sectional view of the spinal connection assembly of FIG. 32, taken along line 34-34 of FIG. 32.

FIG. 41 is a perspective view of an alternative embodiment of the spinal connection assembly of the present invention, having a second bottom-facing opening, together with two posterior spinal connectors.

FIG. 42 is an elevational view of the spinal connection assembly of FIG. 41, taken from line 42-42 of FIG. 41.

DESCRIPTION OF THE INVENTION

Figure 1:
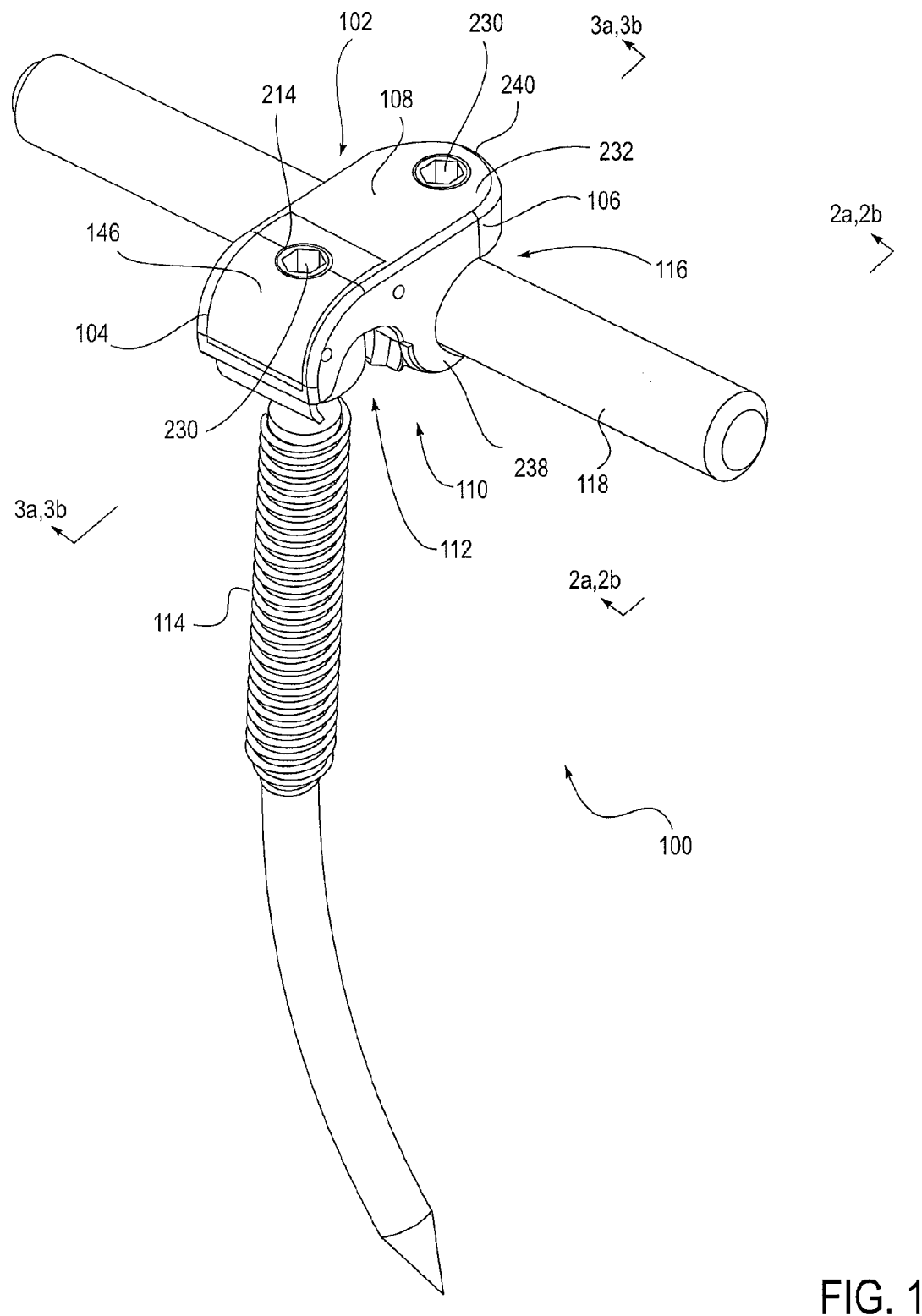
FIG. 1 is a perspective view of an embodiment of the spinal connection assembly of the present invention having a side-facing second opening, together with a posterior spinal connector and a rod.
Figures 2A, 3A:
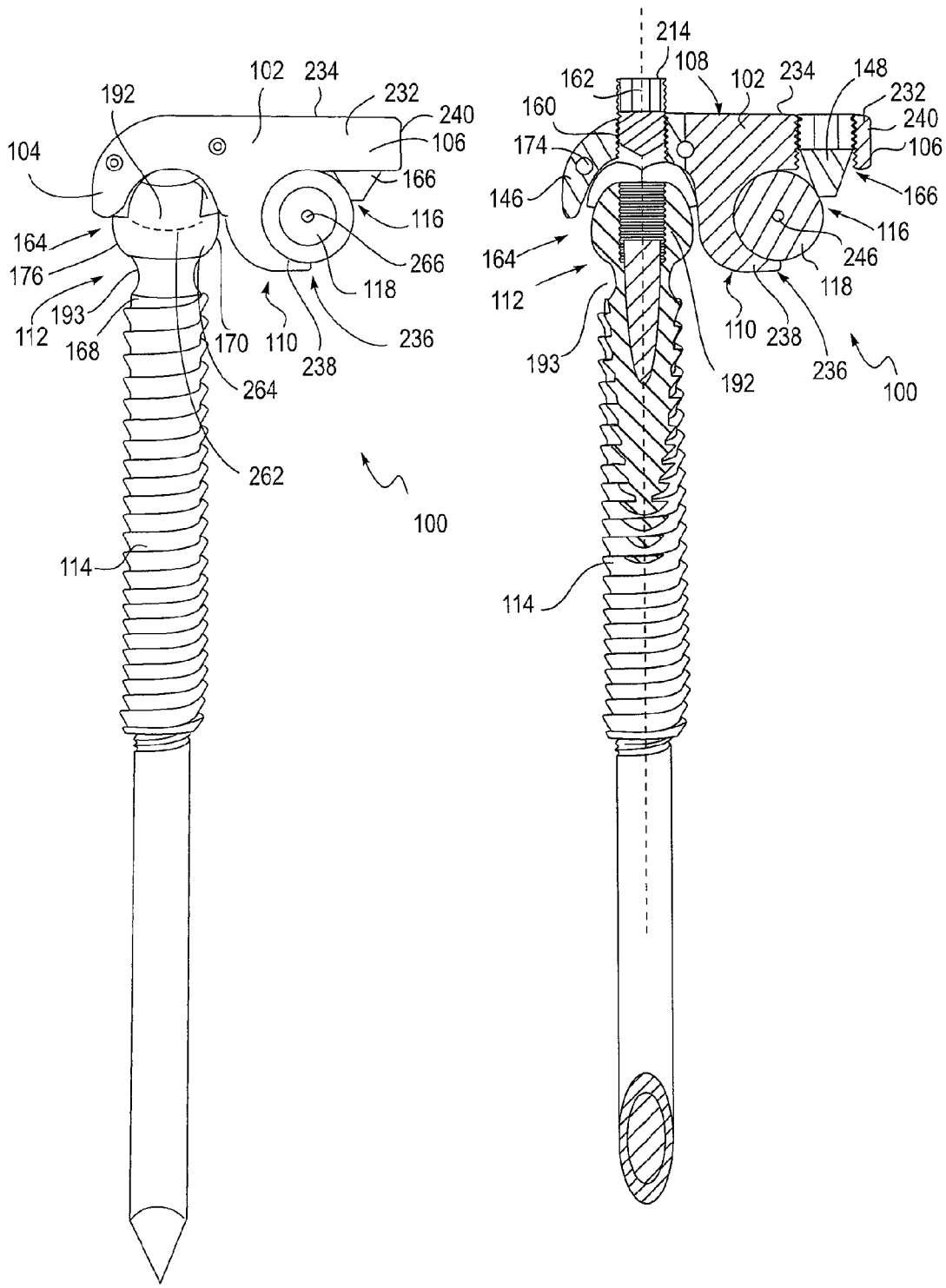
FIG. 2a is side elevational view of the spinal connection assembly of FIG. 1, taken from line 2a-2a of FIG. 1, with the capture elements in an open position.
FIG. 3a is a cross-sectional view of the spinal connection assembly of FIG. 1, taken along line 3a-3a of FIG. 1, with the capture elements in an open position.
Figures 2B, 3B:
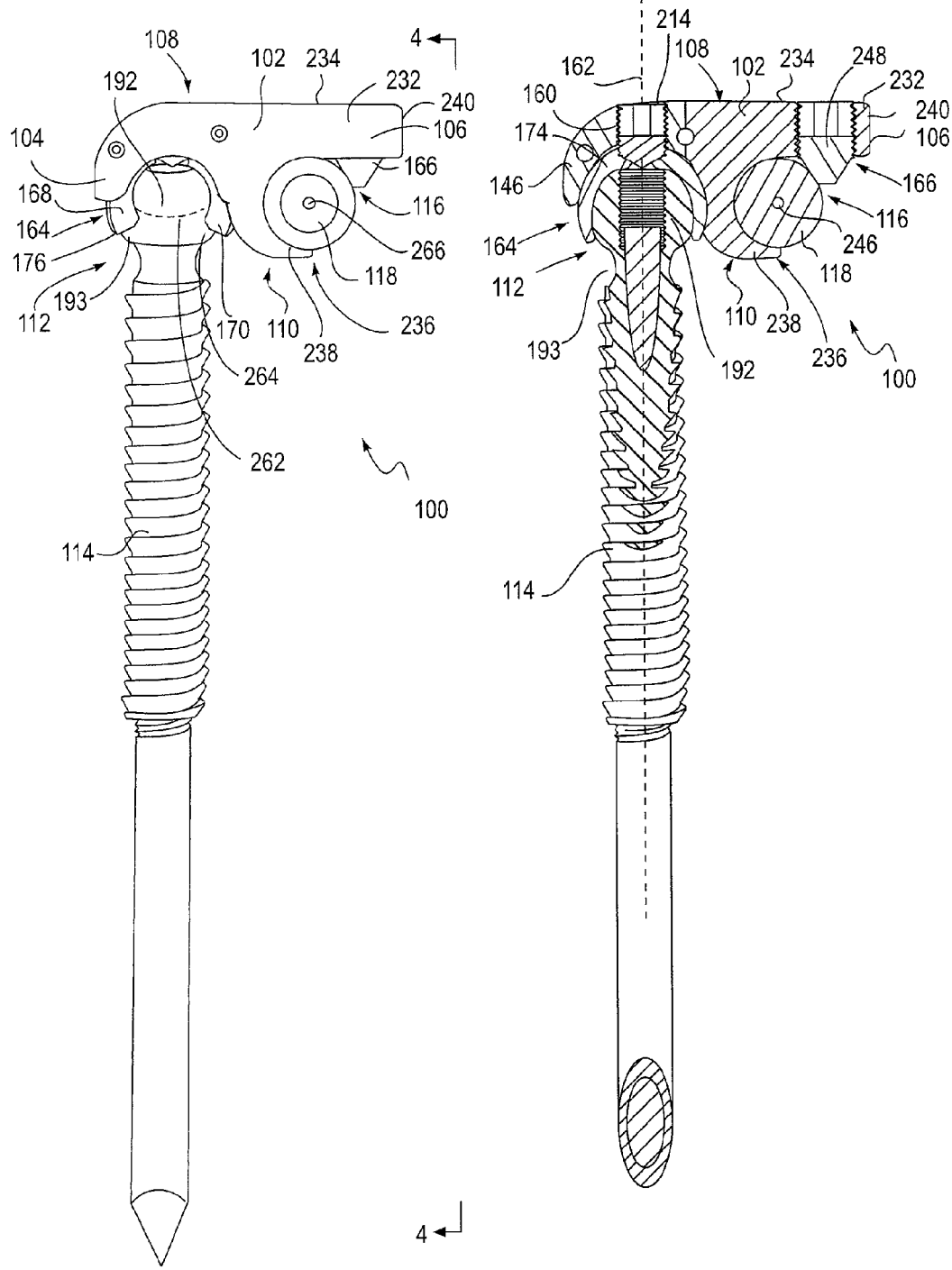
FIG. 2b is side elevational view of the spinal connection assembly of FIG. 1, taken from line 2b-2b of FIG. 1, with the capture elements in a capture position.
FIG. 3b is a cross-sectional view of the spinal connection assembly of FIG. 1, taken along line 3b-3b of FIG. 1, with the capture elements in a capture position.
Figure 4:
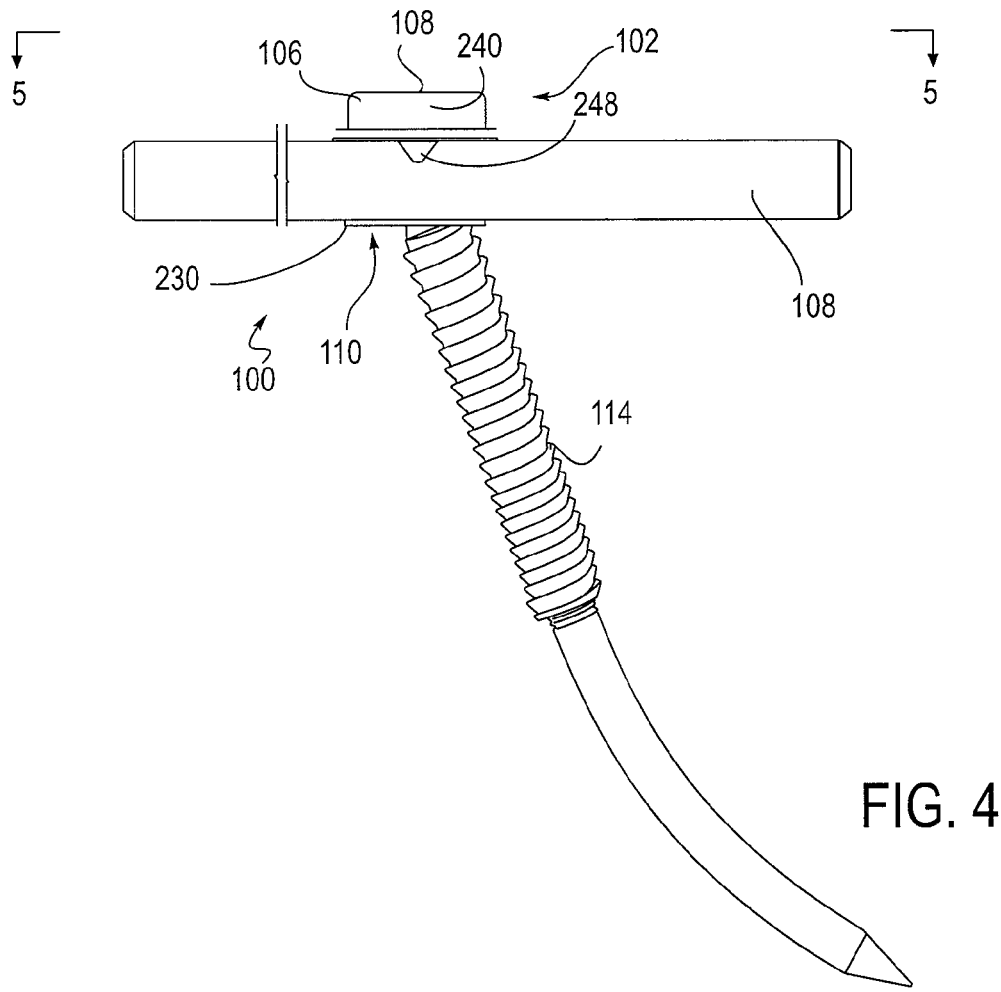
FIG. 4 is a front elevational view of the spinal connection assembly of FIG. 1, taken from line 4-4 of FIG. 2b.
Figure 5:
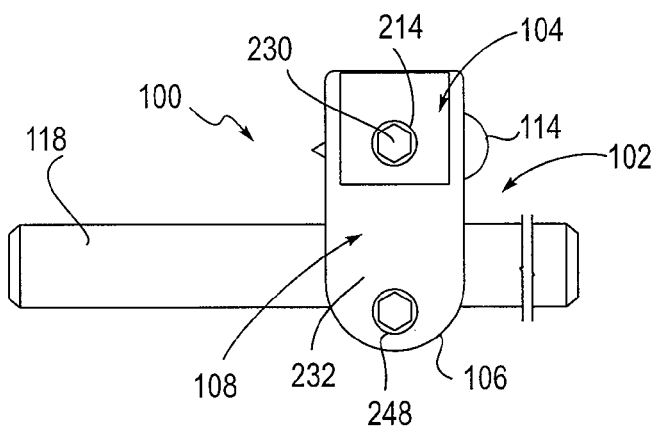
FIG. 5 is a top plan view of the spinal connection assembly of FIG. 1, taken from line 5-5 of FIG. 4.
Figure 6:
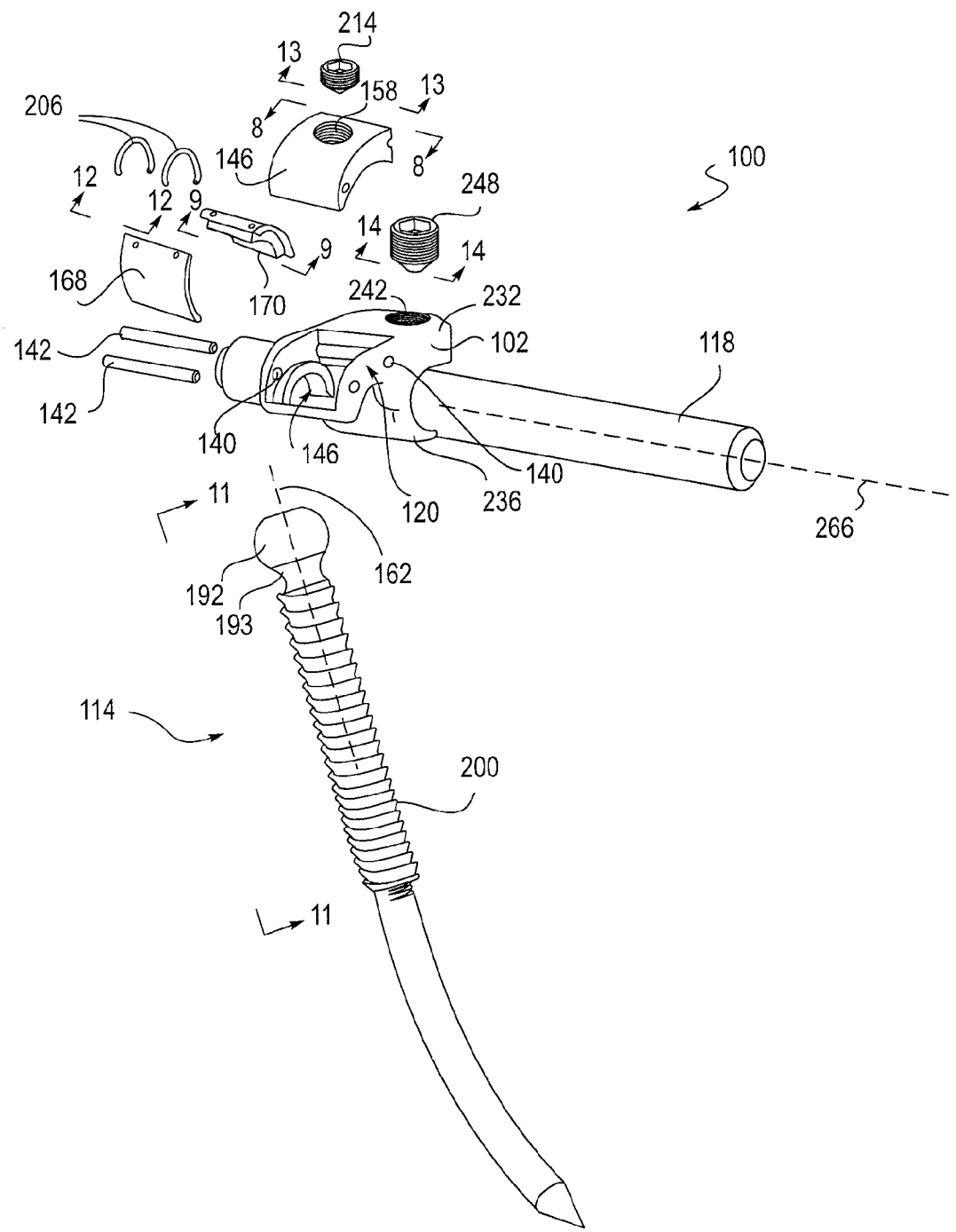
FIG. 6 is an exploded view of the spinal connection assembly of FIG. 1.

The invention is generally directed to a spinal connection assembly. More, specifically, a system for stabilizing adjacent vertebra in the mammalian spine is provided. The system disclosed generally includes a casing or housing having a portion to capture a first connector element, such as but not limited to a posterior spinal connector, and a portion to capture a second connector element, such as but not limited to a rod or second posterior spinal connector.

The spinal connection assemblies described herein and their individual components and respective attachments and securing devices, as well as the rods, posterior spinal connectors and cross-link members described herein may be made of any suitable material for use in the mammalian body, and preferably for use in association with the spine, such as but not limited to, stainless steel, titanium, vitalium, cobalt chrome, nitenol, carbon fiber, polyetheretherketone, plastics, biodegradable materials, bioeluting materials, or combinations of one or more of these materials.

The embodiment of the spinal connection assembly 100 shown in FIGS. 1-14 includes a housing 102 having first and second side portions 104, 106 and a top and a bottom 108, 110. It is noted that the terms "top," "bottom" and "side" are used herein for purposes of discussion only for ease of reference to the various components of the assembly. These terms are not intended, nor provided to indicate any reference to the orientation of the spinal connection assembly as a whole. The first side portion 104 has a bottom-facing first opening 112 adapted for receiving a posterior spinal connector 114. The second side portion 106 is preferably provided with a second opening 116 which is side-facing and which may carry a second securement mechanism or additional securement mechanism or capture mechanism 166 for capturing a connector element, and specifically a rod 118.

Generally, the components of the spinal connection assembly 100 are carried by a housing 102. The housing 102, as shown in FIGS. 1-7, is formed by the first side portion 104 and the second side portion 106. The housing 102 is also formed by the top 108 and bottom 110. The housing 102 includes the opening adapted for receiving the posterior spinal connector 114, namely, the first side portion 104 of the housing 102 has a bottom-facing first opening 112 adapted for receiving a connection element such as posterior spinal connector 114. The first side portion 104 of the housing 102 is formed of an arcuate shaped or downwardly curved portion 120 having first and second sidewalls 122, 124 and an opening 126 there between. A transverse wall 128 or two transverse walls 128, 130 connect the sidewalls. The opening 126 is provided with first and second arcuate guide features 132, 134 or surfaces. Preferably, the first and second arcuate guide surfaces 132, 134 are provided on opposing inner surfaces 136, 138 of the first and second sidewalls 122, 124. A plurality of pin receptors 140 may also be provided through first and second sidewalls 122, 124 of the housing 102 to receive one or more pins 142. A protrusion 144 may also be provided in at least one transverse wall 130.

A nut 146, also known as a cap or a lid, having a body 148 corresponding in shape to opening 126 in the first side portion 104 is received within the opening. The nut 146 preferably has an arcuate portion, or is arcuate in shape, and forms the bottom-facing opening 112 below its, bottom surface 150. The nut 146 also may include a transverse wall 152 having a recess 154 thereon for mating with the protrusion 144 provided on the transverse wall 130 of the housing 102. At least one pin receptor 156 extends transversely through the body 148 of the nut 146 at a position which corresponds to a pin receptor 140 in the housing 102. Preferably, two nut body and housing pin receptors 156, 140 are provided which each receive a pin or capture pin 142. The nut 146 also has a downwardly extending aperture 158, preferably an aperture with an inner thread 160 that extends through the body 148, which is adapted to receive and mate with an outer thread of a screw. The aperture 158 is aligned with the central axis 162 of a posterior spinal connector 114 when received by the assembly 100.

At least one securement mechanism or capture mechanism 164 is carried by the housing 102 for capturing the posterior spinal connector 114 or connector element within an opening 112. As described, the spinal connection assembly 100 includes first and second securement mechanisms or additional securement or capture mechanisms 164, 166. The first securement mechanism or capture mechanism 164 is carried by the first side portion 104 for capturing the posterior spinal connector 114 within the first opening 112. Specifically, the capture mechanism 164 is received between the nut 146 and the first and second arcuate guide surfaces 132, 134 provided on housing 102 on the first side 104. The first securement mechanism 164 is preferably formed at least in part of first and second capture elements 168, 170, also known as leaves or capture arms. The first and second capture elements 168, 170 are disposed in spaced-apart positions within the first opening 112 and are moveable on the respective first and second arcuate guide features 132, 134 between an opened first position, shown in FIGS. 2a and 3a, and a second capture position, shown in FIGS. 2b and 3b.

Figure 9:
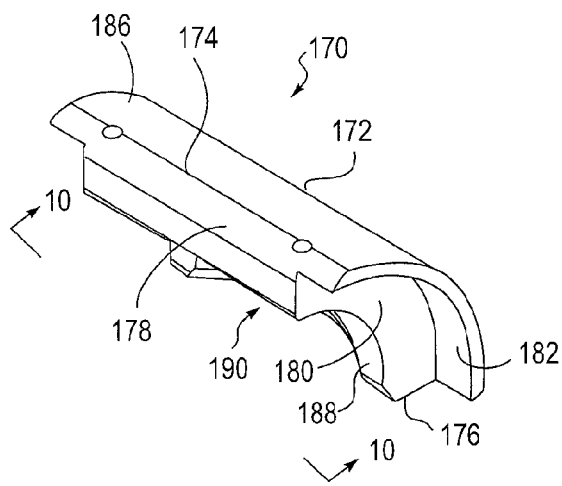
FIG. 9 is a perspective view of a capture element in the spinal connection assembly of FIG. 1, taken from line 9-9 of FIG. 6.
Figure 10:
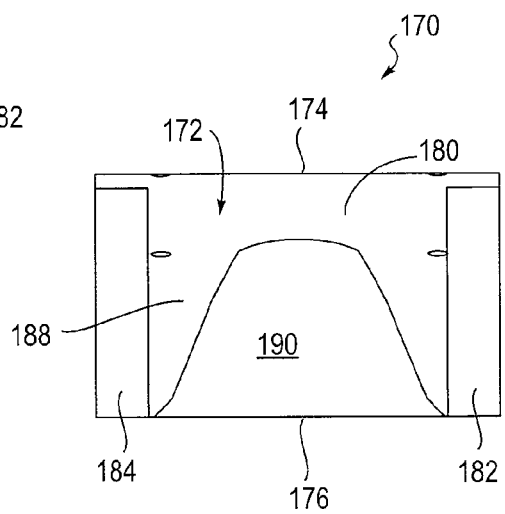
FIG. 10 is an elevational view of the capture element of FIG. 9, taken along line 10-10 of FIG. 9.

Each capture element 168, 170, as shown in FIGS. 9-10, is formed by a body 172 having a top portion 174 and a bottom portion 176, which portions form an outer guide portion 178 and an inner securing portion 180. The outer guide portion 178 preferably has a width that is greater than the width of the inner securing portion 180 so as to be adapted to engage the first and second arcuate guide features 132, 134 or rails. To this end, outer guide portion 178 has a first inner surface 182 adapted to slidably engage the first arcuate guide 132 and a second inner surface 184 adapted to slidably engage the second arcuate guide 134. The outer guide portion 178 preferably has an outer cylindrical surface 186. The first and second surfaces 182, 184 are thus shaped to correspond with the shape of the respective guide features 132, 134 and each preferably has an equivalent radius of curvature. The inner securing portion 180 is formed of or includes an inner surface 188 for engaging a connector element 114 or 118. In one embodiment, as shown in FIGS. 9-10, the inner surface is preferably an inner spherical surface or includes an inner spherical cutout 190 for engaging a spherical portion 192 of a posterior spinal connector 114. Alternatively, the inner surface 188 may be an inner arcuate surface for engaging a transverse member, such as a rod 118.

Figure 11:
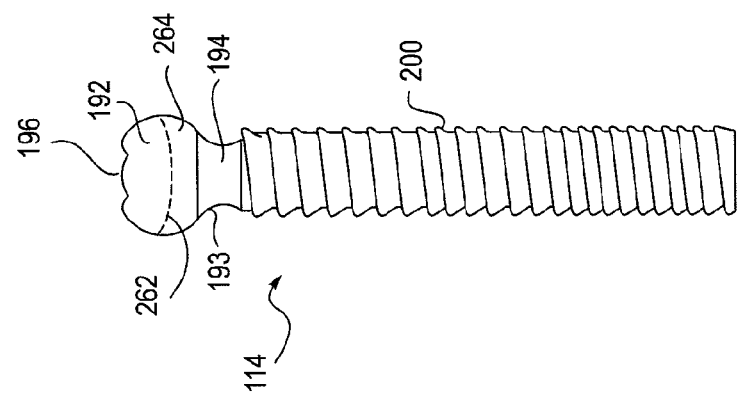
FIG. 11 is an elevational view of a portion of a posterior spinal connector for use with the spinal connection assembly of FIG. 1, taken from line 11-11 of FIG. 6.

The first securement mechanism or capture mechanism 164 preferably engages or secures a posterior spinal connector 114. The posterior spinal connector 114, as shown in FIGS. 2, 3 and 11, has central axis 162 and a portion 192 of the posterior spinal connector 114 is preferably spherical in shape. The posterior spinal connector 114 has a head 192 and a groove 193 adjacent the head for providing a neck 194. More preferably, a portion of the posterior spinal connector 114 or the top portion or head 192 of the posterior spinal connector 114, which is carried by neck 194, is spherical. The portion or head 192 may be engaged by the capture mechanism 164 carried by the first side portion. To this end, the capture mechanism 164 may extend or be extendable at least partially into the groove 193 so as to capture the head 194 within the first opening 112. The head 192 may also include a portion 196 for engaging a tool (not shown) for insertion of the connector 114 into the body. The spinal connector 114 is preferably a screw adapted to engage a bore 198 in a vertebra 199 and may be, for example, a transpedicle screw, lamirio-pedicle screw or a facet screw. As shown in FIG. 11, the screw may include an outer thread 200 along a portion, or posterior portion 202 thereof. An anterior portion 204 having a smooth or roughened surface may also be provided. An exemplary posterior spinal connector 114 suitable for use with the spinal connection assembly 100 is a posterior spinal fastening device having a posterior portion 202 with an external thread 200 and an arcuate anterior portion 204 as described in co-pending U.S. patent application Ser. No. 61/046,762 filed Apr. 21, 2008, the entire content of which is incorporated herein by this reference. While specific examples are given, alternative spinal connection devices suitable for the purposes provided herein are also contemplated for use in association with the spinal connection assembly and assemblies described herein.

The spinal connection assembly and assemblies described herein may also be used with alternative connector elements to treat a spine of a mammalian body. Acceptable connector elements may include a screw as set forth above, or may alternatively include a device which interconnects adjacent screws, assemblies and devices, and thus vertebra, such as a rod 118 or transverse member. Transverse member or rod 118 may be any rod suitable for use in the mammalian body, and in particular in association with the mammalian spine and interconnecting vertebra. For example, a suitable rod may be a cylindrical rod 118 of any suitable length.

Figure 12:
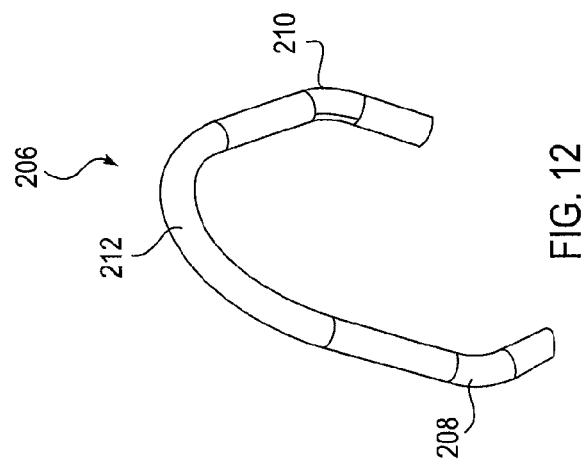
FIG. 12 is a spring clip for use with the spinal connection assembly of FIG. 1, taken from line 12-12 of FIG. 6.

Capture elements 168, 170 of the first securement mechanism 164, which secures to the posterior spinal connector 114, may be biased away from an engagement or securing position by a spring or clip 206, and preferably a plurality of such springs or clips. In the embodiment shown in FIGS. 2a-b, two spring clips 206 are provided for operable engagement with the first and second capture elements 168, 170 and may connect the capture elements. As shown in FIG. 12, each spring clip 206 has a first arm 208 integrally connected to a second arm 210. Each of the first and second arms 208, 210 is shaped to engage the corresponding first and second capture elements 168, 170. The top portion 212 of the spring clip 206 is arranged to bias the first and second arms 208, 210, so as to force the first and second capture elements 168, 170 toward an open or rest position in which the top portions 174 of each of the capture elements are in close relationship. Each of the spring clips 206 cooperates with the arcuate guide features 132, 134 in the first opening 112 of the housing 102, and is capable of assisting in the radial movement of the capture elements along the guides.

Figure 13:
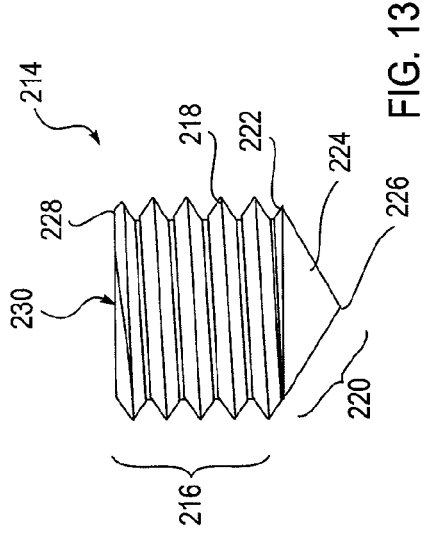
FIG. 13 is a capture element for use with the spinal connection assembly of FIG. 1, taken from line 13-13 of FIG. 6.

The first securement mechanism 164 further includes a limiting element 214. Limiting element 214 is aligned with the central axis 162 of the posterior spinal connector 114 and included for restricting axial travel of the posterior spinal connector 114 within the housing 102. A capture screw is provided in one embodiment as a limiting element 214 which engages the first and second capture elements 168, 170 and moves the capture elements between the first open position and second engaged position. To this end, the limiting element 214 or capture screw is a threaded connector that mates with a corresponding thread 160 on the housing 102 or in the nut 146. The capture screw 214, as shown in FIG. 13, is a cylindrical screw having an outer threaded portion 216 including an outer thread 218 for engaging the inner thread 160 of the threaded aperture 158 in the nut 146. The outer threaded portion 216 preferably has a length which corresponds to the depth of the nut 146 and depth of the aperture. The capture screw 214 also carries an engaging portion 220 at its anterior end 222. Preferably, the engaging portion 220 has an inwardly tapered or conical portion 224 terminating at a tip 226. The inwardly tapering portion 224 outer surface is adapted to engage the upper portion 174 of the first and second capture elements 168, 170. The posterior portion 228 of the capture screw 214 may include a tool engaging portion 230 for use in rotatably inserting the screw.

In a preferred embodiment, the first securement mechanism 164 is configured to permit the posterior spinal connector 114 to pivot in a plane through an angle ranging from 0 to 180 degrees relative to the housing 102. More preferably, the capture elements are configured to permit the posterior spinal connector 114 to pivot in the plane through an angle of at least 60 degrees relative to the housing 102. In addition, the capture elements 168, 170 are configured to permit the posterior spinal connector 114 to pivot in an additional plane orthogonal to the first-named plane through an angle ranging from 0 to 120 degrees relative to the housing 102. Even more preferably, the capture elements 168, 170 are configured to permit the posterior spinal connector 114 to pivot in the additional plane through an angle of at least 60 degrees relative to the housing 102. More preferably, the capture elements 168, 170 are configured to permit the posterior spinal connector 114 to rotate 360 degrees about an axis extending in the first-named and additional planes.

Figure 7:
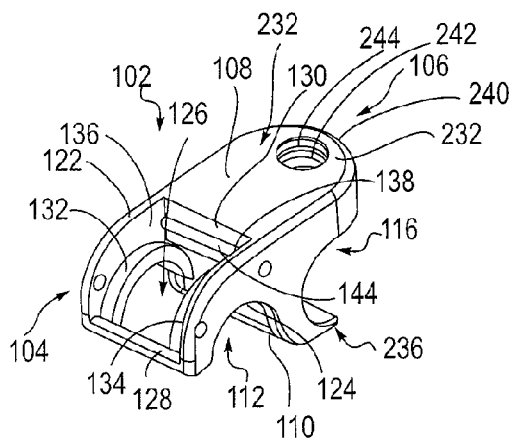
FIG. 7 is a perspective view of the housing of the spinal connection assembly shown in FIG. 6.
Figure 8:
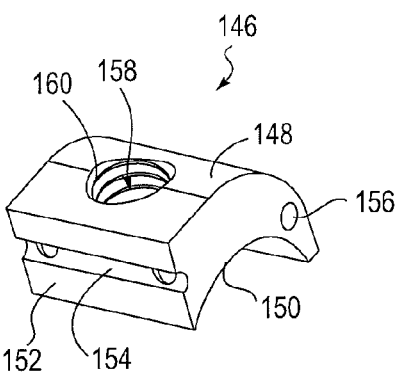
FIG. 8 is a perspective view of a nut in the spinal connection assembly of FIG. 1, taken from line 8-8 of FIG. 6.

The second side portion 106 of the housing 102 is provided with a second opening, in the illustrated embodiment a side-facing opening 116, and may carry a second securement mechanism or additional securement mechanism or capture mechanism 166 for capturing a connector element, which may be a posterior spinal connector or a rod. In the embodiment shown in FIGS. 1-7, the connector element is a cylindrical rod 118. More specifically, the second side portion 106 of the housing 102 has a top portion 232 which has a substantially planar top surface 234. The second side portion 106 also has a bottom portion 236 which includes an arcuately extending arm 238. The arcuately extending arm 238 in combination with the top portion 232 preferably forms the side-facing receptor or opening 116 having a radius corresponding to the radius of the cylindrical rod 118. The end 240 of the second side portion 106, as shown in FIG. 7, may include an outwardly curved portion. An aperture 242 is positioned through the top 232 of the second side portion 106 of the housing 102. The aperture 242 preferably has an inner thread 244 for mating with a screw. The aperture 242 is also preferably positioned off-center from the central axis 246 of the opening 116, and thus, the rod 118 received therein. Preferably, the aperture 242 is positioned toward the end 240 of the second side portion 106.

Figure 14:
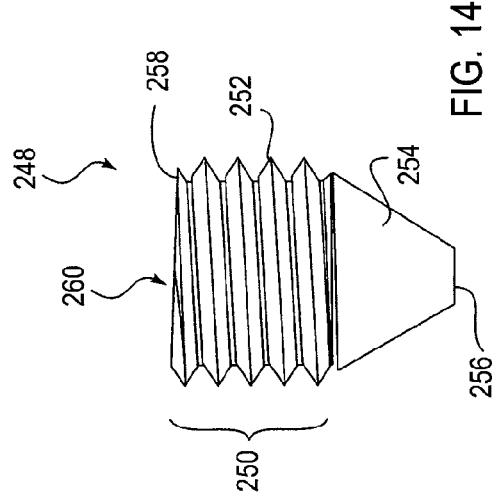
FIG. 14 is a capture element for use with the spinal connection assembly of FIG. 1, taken from line 14-14 of FIG. 6.

The second side portion 106, and specifically the aperture 242 in the side portion, receives a threaded connector or screw such as a second capture screw 248. As shown in FIG. 14, second capture screw 248 may include a threaded portion 250 having an outer thread 252 that is adapted to engage the inner thread 244 of the aperture 242. The second capture screw 248 has an inwardly tapered or conical portion 254 at its anterior end terminating at a tip 256. The length of the threaded portion 250 of the second capture screw 248 preferably corresponds to the depth of the aperture 242 in the second side portion 106, so that the inwardly tapered end 254 of the screw extends beyond the aperture and is capable of engagement with the rod 118 received in the opening 116. The threaded portion 250, at its posterior end 258, also may include a tool engaging portion 260 for use in inserting the second capture screw 248.

The spinal connection assembly 100 may be generally formed or assembled by assembling the first securement mechanism 164 in the opening 126 on the first side portion 104 of the housing 102 (see FIGS. 1-6). More specifically, the guide portion 178 of each of the first and second capture elements 168, 170 is placed in contact with each of the arcuate guide features 132, 134 attached to the housing 102. The spring clips 206 may be engaged with the capture elements 168, 178 so as to bias the capture elements toward a rest position on the guide features. The first and second capture elements 168, 170 are disposed in spaced-apart positions within the first opening 112, but have their top portions 174 in a close relationship. The capture elements are then moveable on the respective first and second arcuate guide features 132, 134 from an opened first position, or rest position, for receiving a portion of, and preferably the head 192 of the posterior spinal connector 114, and a second position for capturing the head 192 of the posterior spinal connector 114.

Subsequently, nut 146 is placed over the opening 126 in the first side portion 104 of the housing 102 to cover the opening, and form the bottom-facing first opening 112. One or more pins 142 may then be inserted into the one or more receptors 140 in the housing 102 and receptors 156 in the attached nut 146 to secure the nut 146 to the housing 102. The posterior spinal connector 114 or connector element is then placed in the bottom-facing opening 112 of the first side portion 104 of the housing 102 between the first and second capture elements 168, 170. Specifically, the head or spherical head 192 of the posterior spinal connector 114 is received by the securing portion 180 of each of the capture elements. Because the capture elements in their home or rest position are at or above the equator 262 of the screw head 192, this allows the screw head 192 to be placed within the casing or housing 102.

The limiting element or capture screw 214 is then inserted into aperture 158 in the top portion 108 of the housing 102, or more specifically into nut 146, and rotationally inserted into the opening by a tool (not shown) until it engages the first and second capture elements 168, 170. As insertion continues, the top portions 174 of each of the capture elements travel along the anterior tapered portion 224 of the capture screw 214. Accordingly, as the capture screw 214 is inserted or moved further downward, the engagement of the capture elements with the anterior portion of the screw causes the top portions 174 of each of the capture elements 168, 170 to move apart, forcing the capture elements to slidably travel along the arcuate guide features 132, 134 on the housing 102 and causing the lower portions 176 of the capture elements to move downward and inward, thus moving the lower portions beyond the equator 262 of the spherical shaped head 192 so as to engage the lower portion 264 of the spherical head 192 of the posterior spinal connector 114. As the capture screw 214 is advanced, it first urges the arms or capture elements 168, 170 apart against the force of the springs 206, then ultimately engages the screw head 192 and secures it against the arms 168, 170. The capture screw 214 continues to travel until it contacts the head 192 of the posterior spinal connector 114, thus restricting axial travel of the posterior spinal connector 114. In this manner, the posterior spinal connector 114 is secured in place in the opening by both the capture screw 214 and the first and second capture elements 168, 170. When necessary, the capture screw 214 may be backed out or removed, wherein the springs 206 cause the arms or capture elements' top portions 174 to move back toward one another as they move upwardly into the housing 102, allowing the screw head 192 to be pulled out of the housing 102.

A second connector element, such as a rod 118, may be connected to the second side portion 106 of the housing 102. The rod 118 is arranged so that it may be received by the housing's second side portion 106, formed by the arcuate arm 238 and top portion 232 of the second side portion 106. Specifically, the rod 118 is oriented so that it may fit lengthwise within the opening wherein its central axis 266 is generally perpendicular to the central axis 162 of the posterior spinal connector 114. The rod 118 is inserted into the opening 116. Then, limiting element or second capture screw 248 is inserted into the aperture 242 extending through the top portion 232 of the second side portion 106. The screw 248 is rotationally inserted into the aperture 242 by a tool (not shown). Rotation and travel of the screw continues so as to place the anterior tapered or conical portion 254 of the screw in contact with the rod 118. Travel of the screw stops when the anterior tapered portion 254 forms a friction fit engagement with the rod 118, thereby retaining the rod 118 in place in the opening 116. Preferably, the second capture screw 248 engages the rod 118 off-center from the central axis 266 of the rod 118 and on an outer surface of the rod 118.

Figure 15:
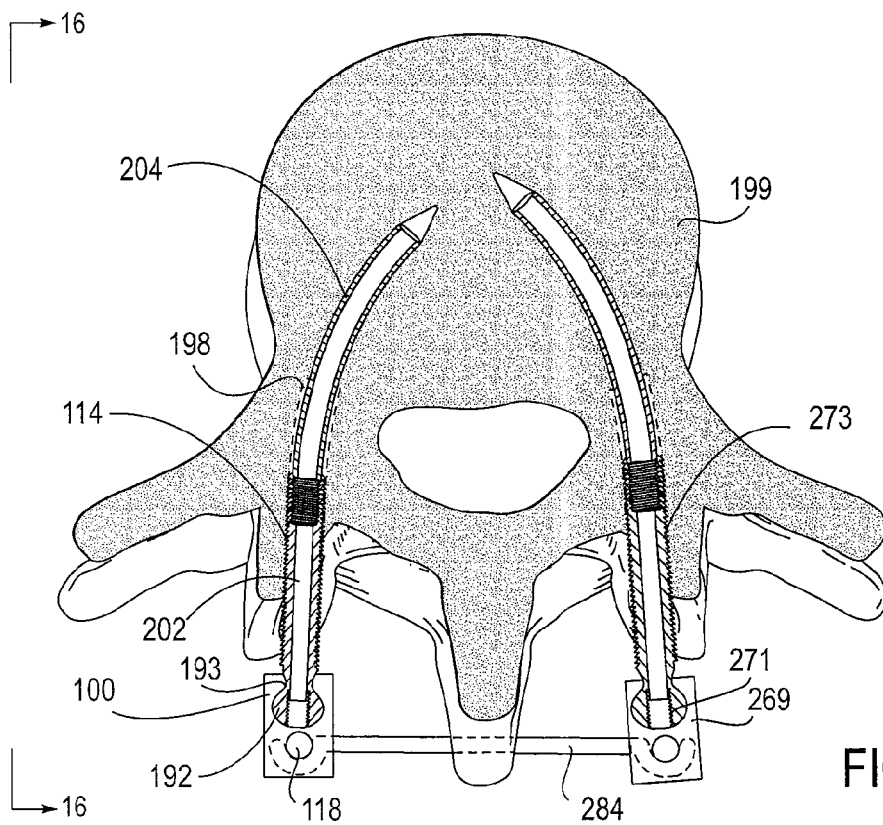
FIG. 15 is a plan view showing the spinal connection assembly of FIG. 1 placed in a vertebra in a transpedicular orientation.
Figure 16:
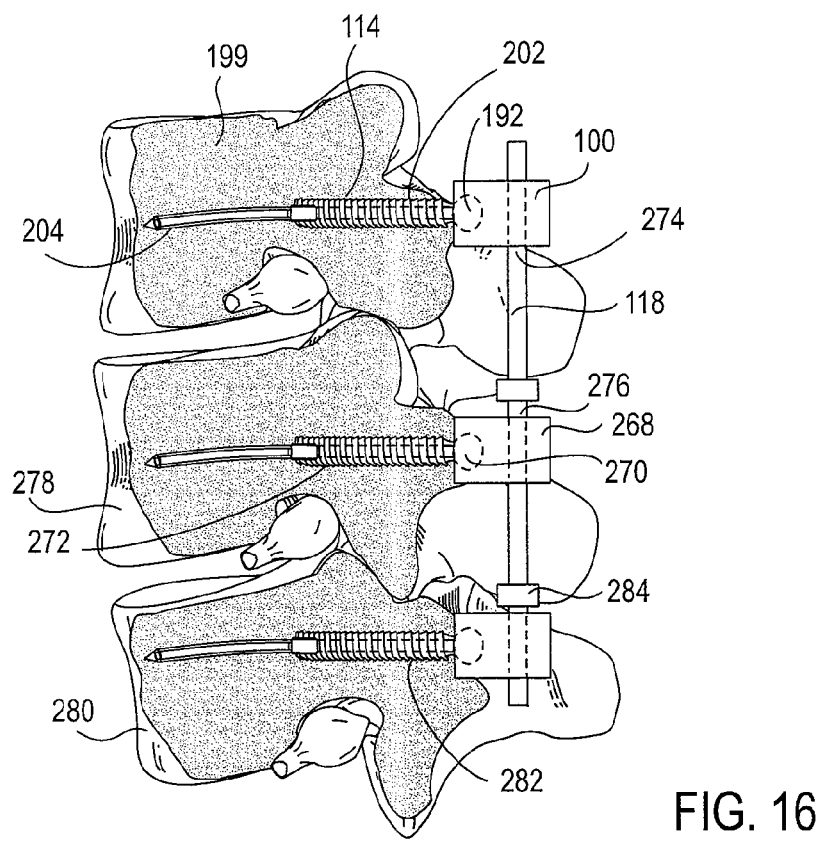
FIG. 16 is an elevational view showing the spinal connection assembly of FIG. 1 placed in a vertebra in a transpedicular orientation, taken from line 16-16 of FIG. 15, together with additional spinal connection assemblies placed in adjacent vertebra in a transpedicular orientation and a rod.
Figure 17:
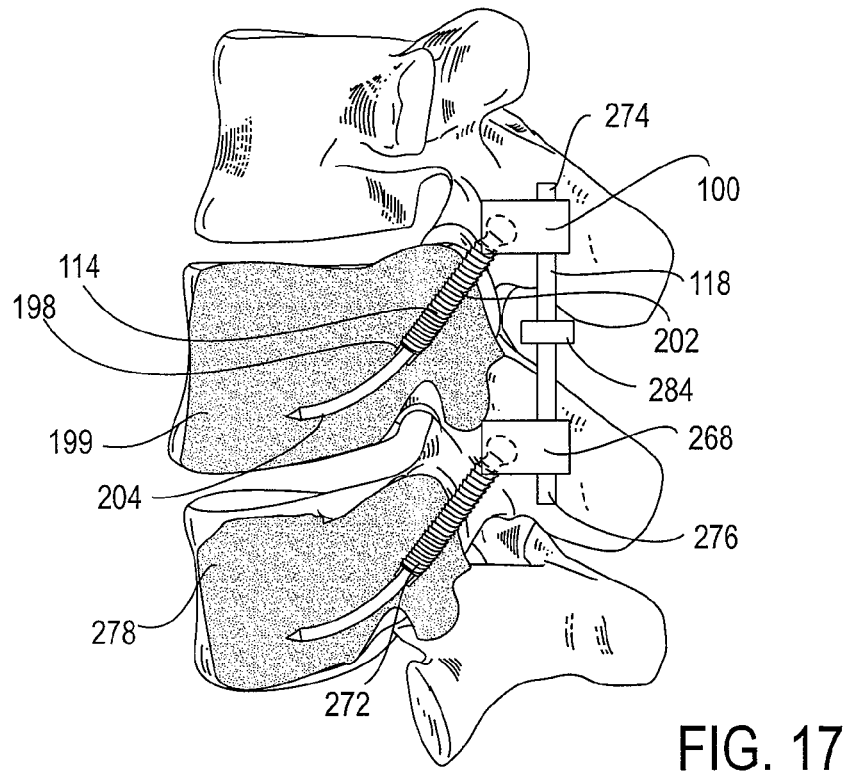
FIG. 17 is an elevational view of the spinal connection assembly of FIG. 1, placed in a vertebra in a laminopedicular orientation together with an additional spinal connection assembly placed in an adjacent vertebra in a laminopedicular orientation.
Figure 18:
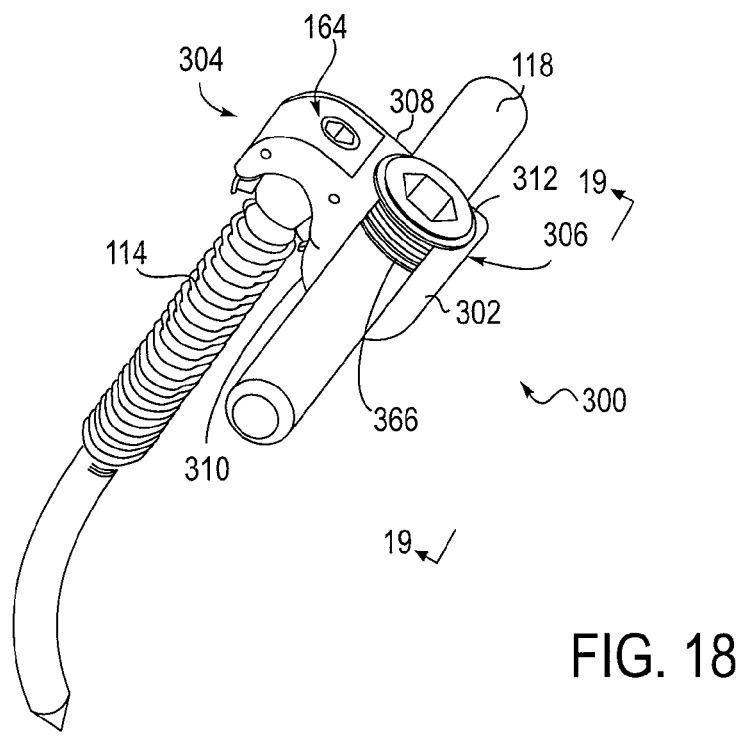
FIG. 18 is a perspective view of an alternative embodiment of the spinal connection assembly of the present invention, having a top-facing second opening, together with a posterior spinal connector and a rod.
Figure 22:
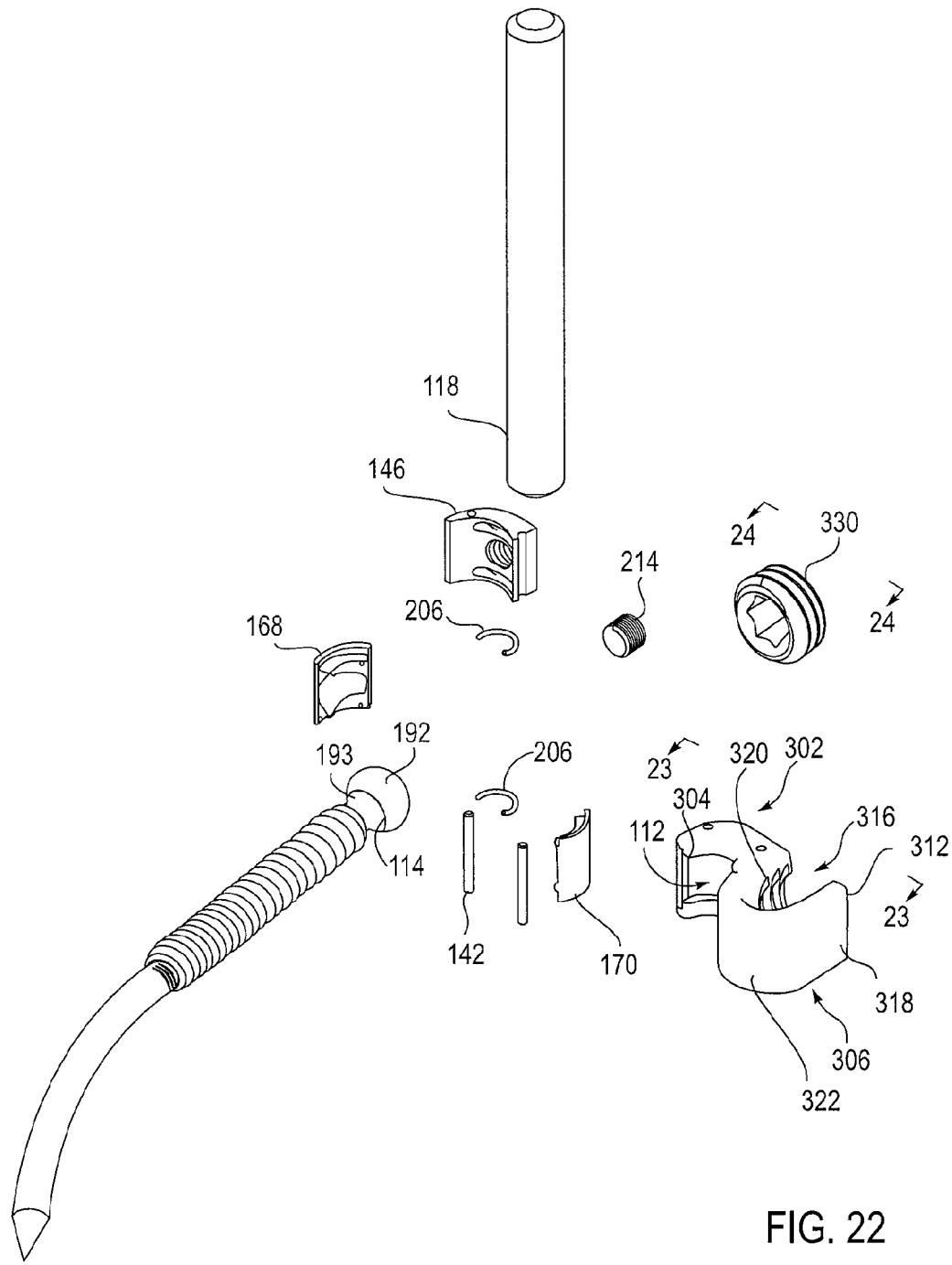
FIG. 22 is an exploded view of the spinal connection assembly of FIG. 18.
Figure 23:
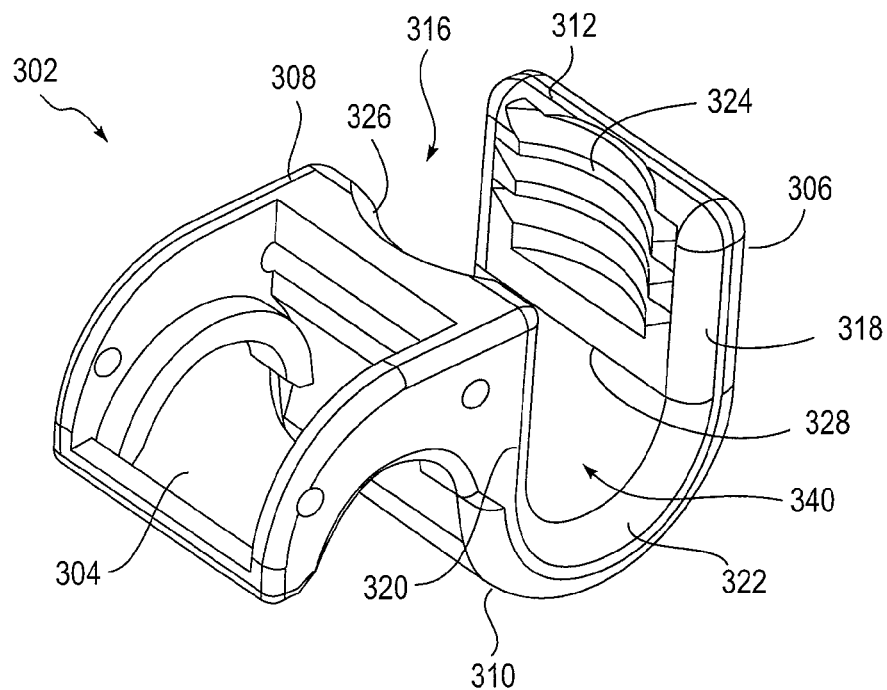
FIG. 23 is a perspective view of the housing of the spinal connection assembly shown in FIG. 18, taken from line 23-23 of FIG. 22.
Figure 24:
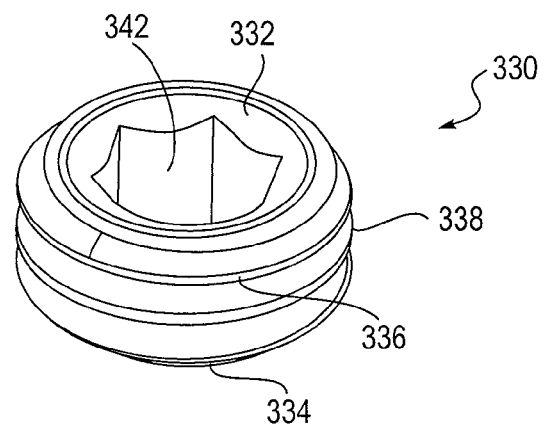
FIG. 24 is a perspective view of a body screw in the spinal connection assembly shown in FIG. 18, taken from line 24-24 of FIG. 22.
Figure 25:
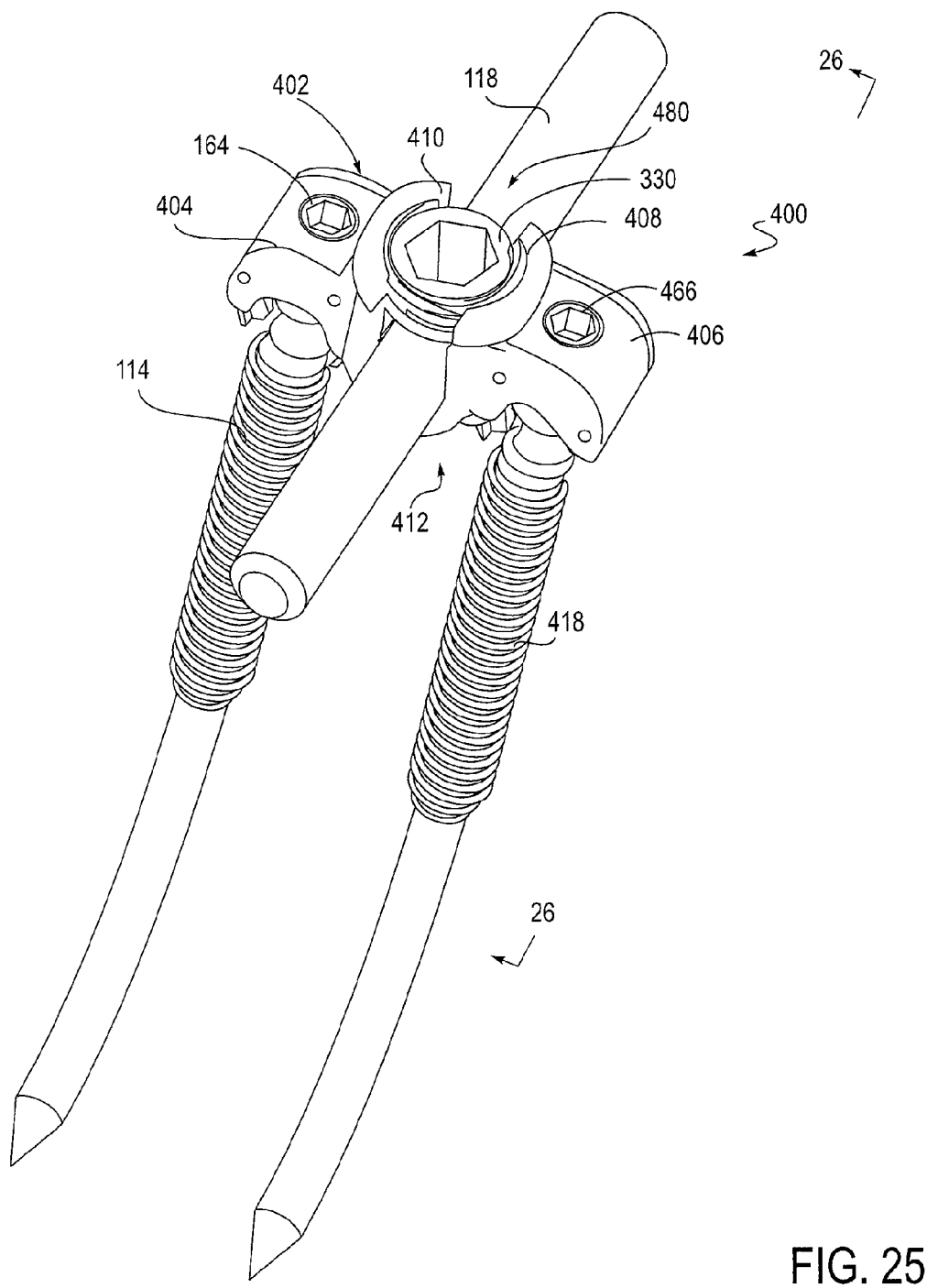
FIG. 25 is perspective view of an alternative embodiment of the spinal connection assembly of the present invention, having a top-facing opening in a center portion, together with two posterior spinal connectors.
Figure 26:
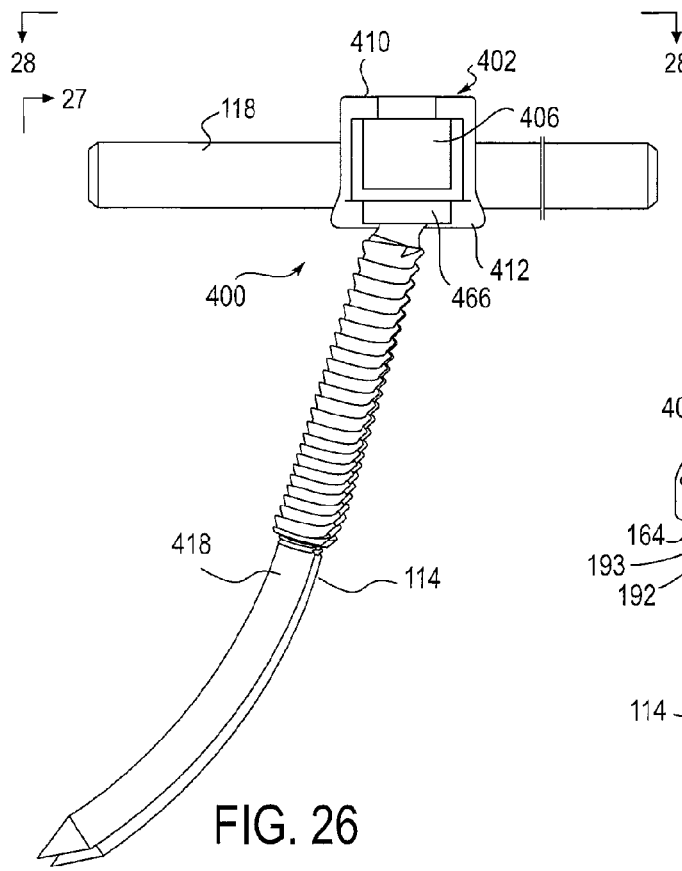
FIG. 26 is an elevational view of the spinal connection assembly of FIG. 25, taken from line 26-26 of FIG. 25.
Figure 27:
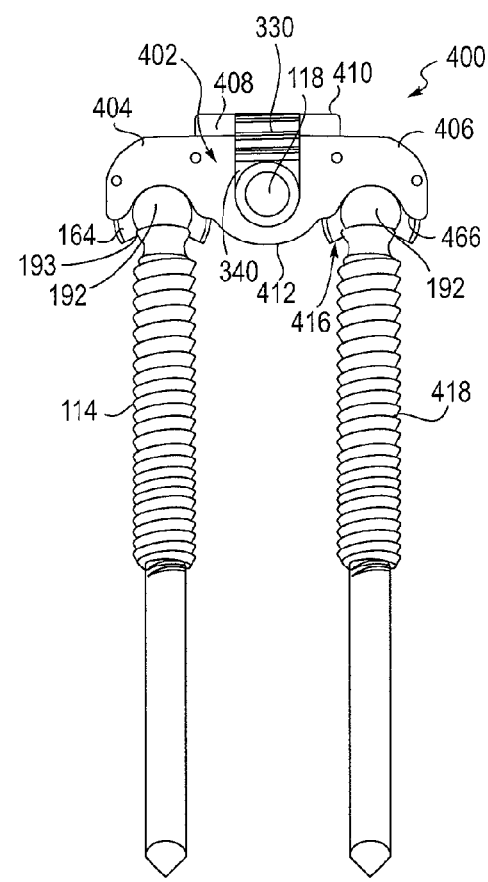
FIG. 27 is an elevational view of the spinal connection assembly of FIG. 25, taken from line 27-27 of FIG. 26.
Figure 28:
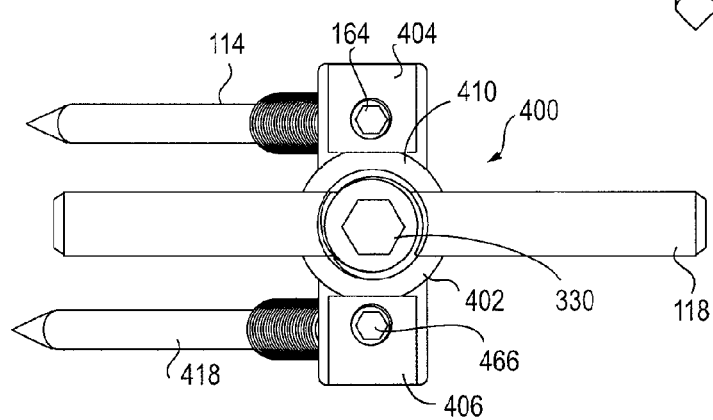
FIG. 28 is a plan view of the spinal connection assembly of FIG. 25, taken from line 28-28 of FIG. 26.
Figure 29:
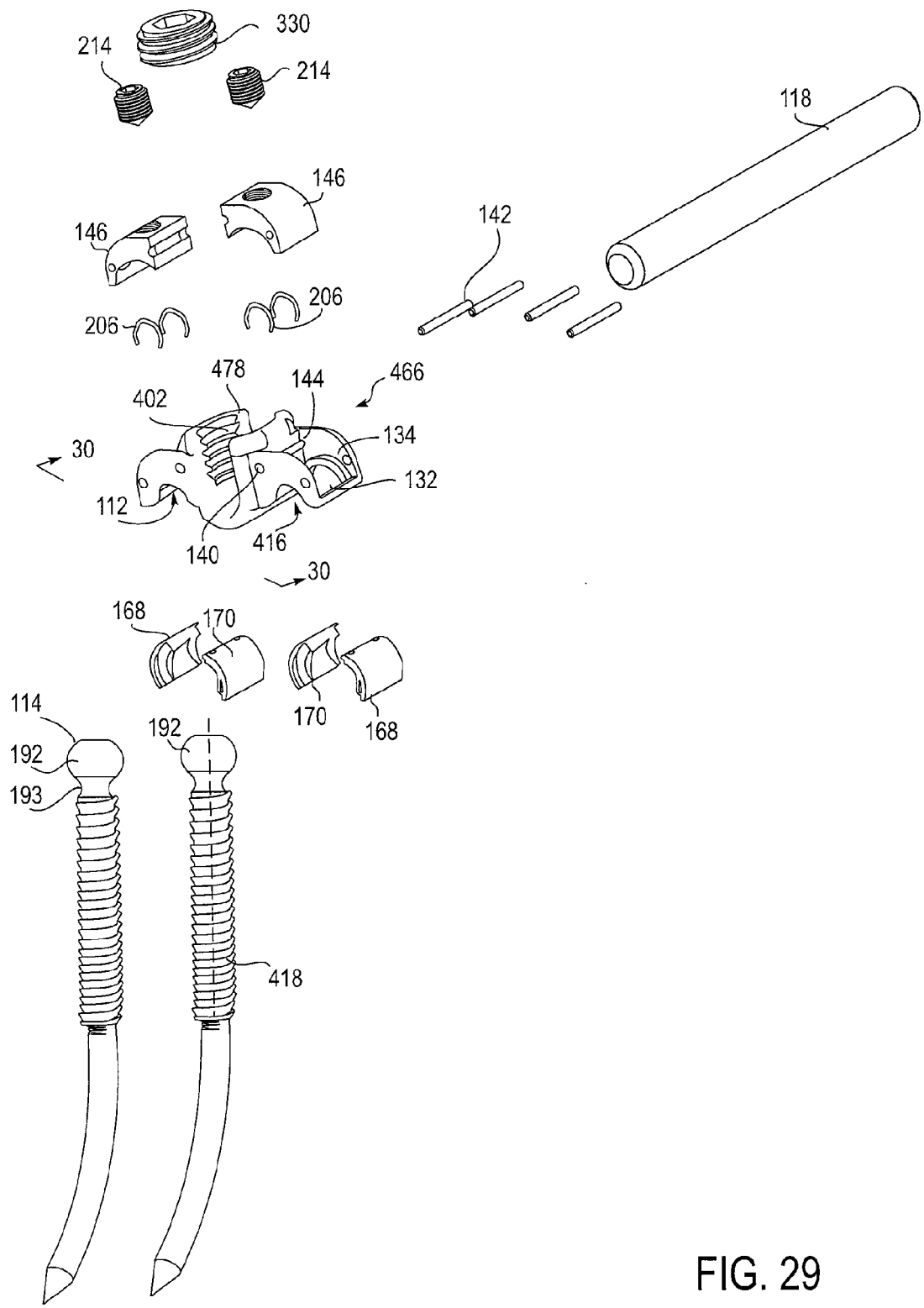
FIG. 29 is an exploded view of the spinal connection assembly of FIG. 25.
Figure 30:
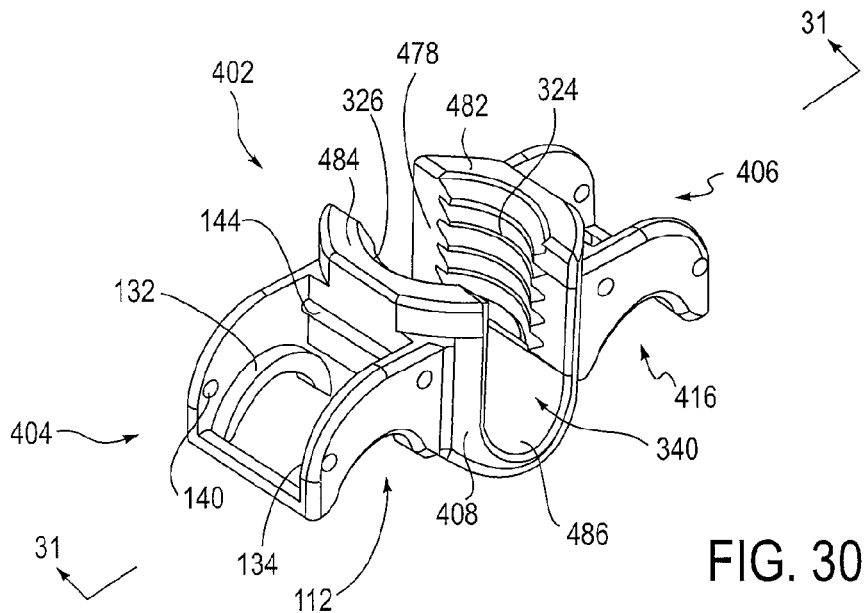
FIG. 30 is a perspective view of the housing of the spinal connection assembly of FIG. 25, taken from line 30-30 of FIG. 29.
Figure 31:
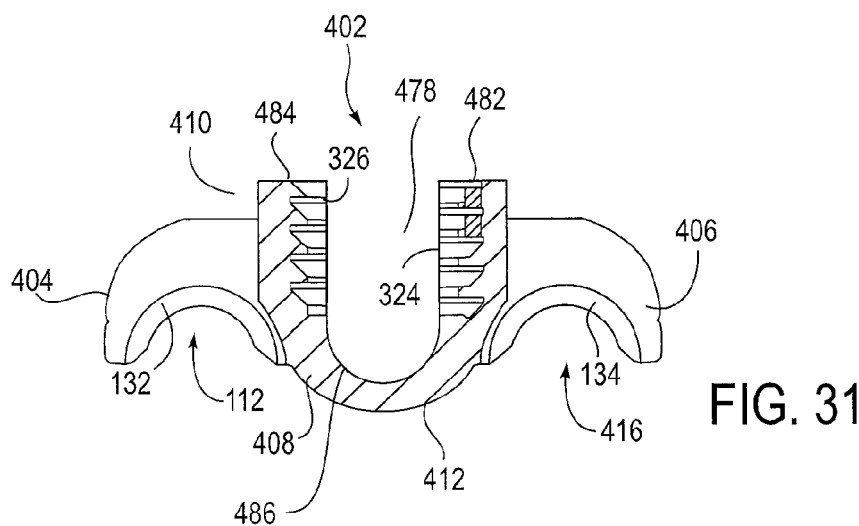
FIG. 31 is a cross-sectional view of the housing of the spinal connection assembly shown in FIG. 30, taken along line 31-31 of FIG. 30.
Figure 32:
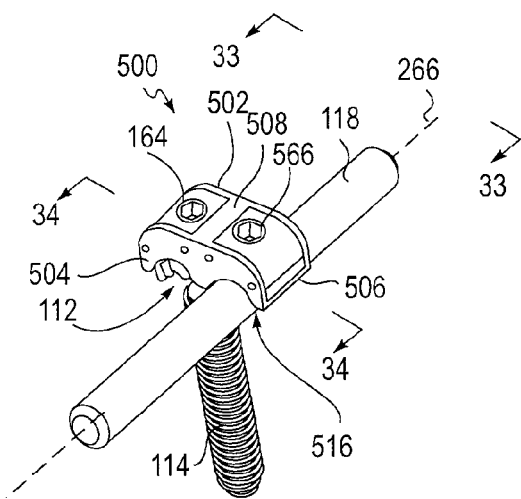
FIG. 32 is a perspective view of an alternative embodiment of the spinal connection assembly of the present invention, having a bottom-facing second opening, together with a posterior spinal connector and a rod.
Figure 36:
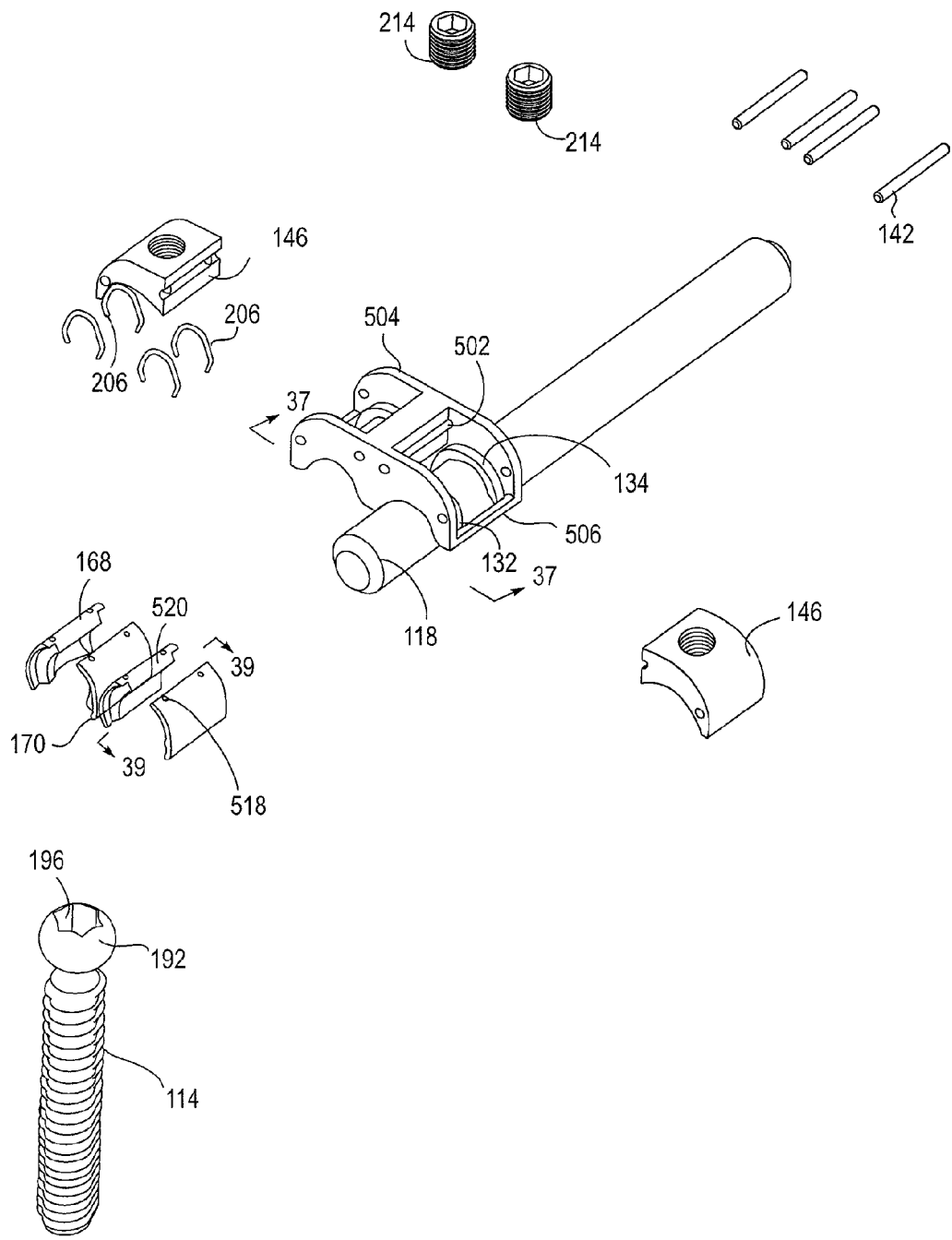
FIG. 36 is an exploded view of the spinal connection assembly of FIG. 32.
Figures 35, 37, 38:
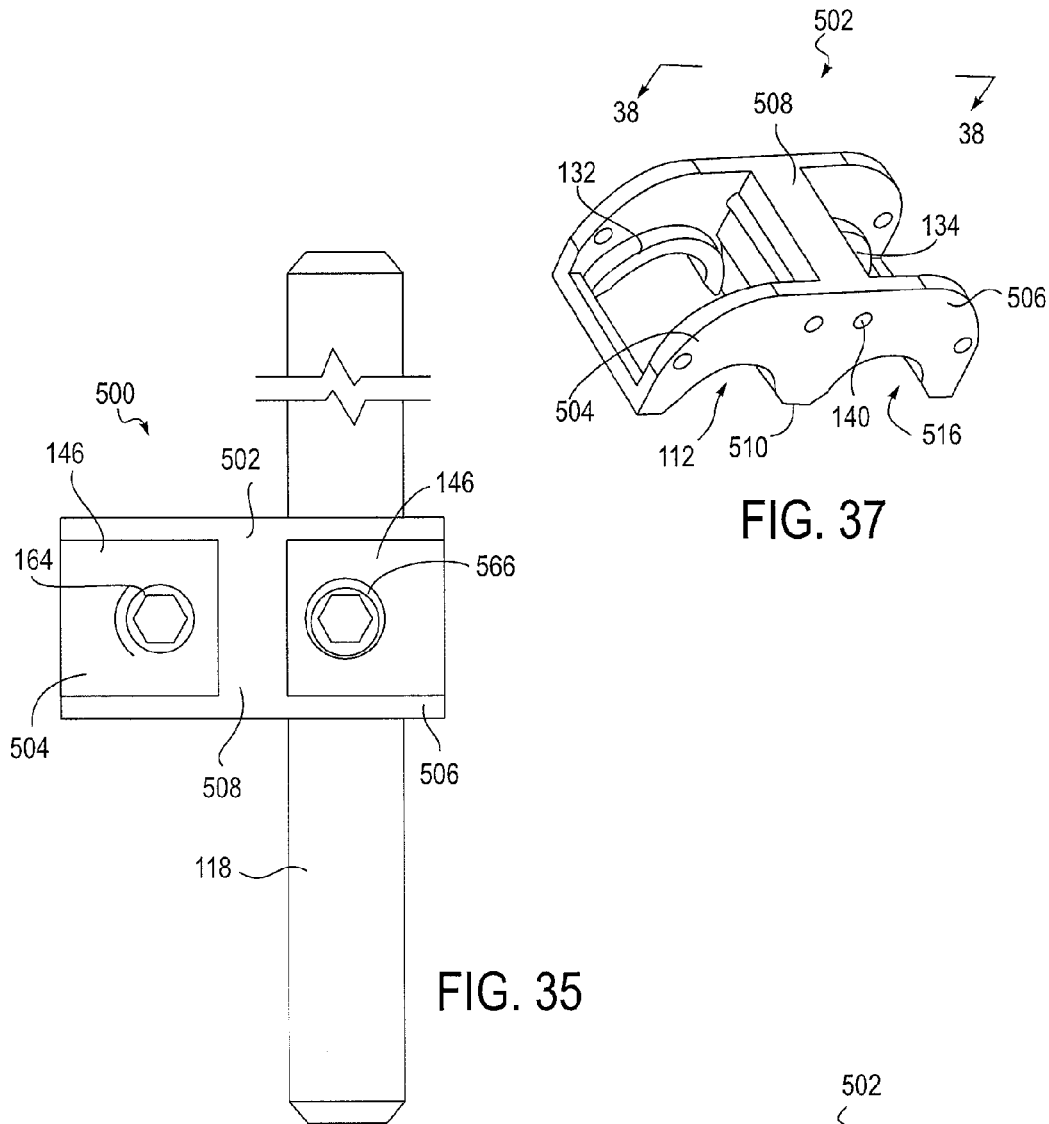
FIG. 35 is a plan view of the spinal connection assembly of FIG. 32, taken from line 35-35 of FIG. 33.
FIG. 37 is a perspective view of the housing of the spinal connection assembly of FIG. 32, taken from line 37-37 of FIG. 36, absent a rod.
FIG. 38 is a plan view of the housing of the spinal connection assembly shown in FIG. 32, taken along line 38-38 of FIG. 37.

In use, as shown in FIGS. 15-17, one or more posterior spinal connectors 114 is placed into the vertebra 199 by any means known in the art. The posterior spinal connector 114 may be inserted in a variety of manners into the vertebra, such as transpedicular (see FIG. 15-16), laminopedicular (see FIG. 17), or transfacet or any combination of the foregoing. Subsequently, the spinal connection assembly 100 may be connected as described, by placing the head 192 of the posterior spinal connector 114 into the bottom-facing opening 112 in the housing 102 and locking the securement mechanism 164 over the head 192 of the posterior spinal connector 114 as described herein.

More than one posterior spinal connector may be attached to a vertebra 199 (see FIG. 15) or adjacent vertebra 278, 280 (see FIG. 16-17). Each respective posterior spinal connector may carry a spinal connection assembly 100 on its head. Specifically, as shown in FIGS. 16-17, a first spinal connection assembly 100 may be attached to a first posterior spinal connector 114 in the manner described herein. A second spinal connection assembly 269 may be attached to the head 271 of a second posterior spinal connector 273, in the manner described herein with respect to the first spinal connection assembly 100. The first and second spinal connection assemblies may each further be interconnected in more than one arrangement by the attachment of a connector element which extends between the first spinal connection assembly 100 and a second spinal connection assembly 268 or 269. For example, as can be seen in FIGS. 15 and 16, a first portion 274 of the rod 118 is received by the first spinal connection assembly 100 within the opening in the second side portion 106 of the housing 102, for example the side-facing opening 116, thereof, and secured in place by rotational insertion of the capture screw 214 to a locking or engaged position (see FIG. 3b). A second portion 276 of the rod 118 is received by the second spinal connection assembly 268 within the opening in the second side portion of the housing (see FIG. 16), and secured in place by rotational insertion of the capture screw to a locking or engaged position in the same manner. In this position, the first and second spinal connection assemblies 100, 268, and thus posterior spinal connectors 114, 272, are interconnected or locked together. As can be best seen in FIG. 15, cross-linking members 284 may also be added, by engaging the ends thereof to the rod 118, so as to interconnect adjacent posterior spinal connectors 100, 269 located in the same vertebra 199. It is also contemplated that alternative embodiments of spinal connection assemblies may be interconnected or locked together by the transverse member or rod 118. Additional assemblies may be connected in the same or a different manner.

FIG. 17 illustrates laminopedicular insertion of the posterior spinal connector 114, 272 into adjacent vertebra. The spinal connection assemblies 100, 268 are attached in the same manner as described with respect to the transpedicular insertion of FIG. 16, and may include rod 118 and cross-link 284 connected as described, the primary difference being the location of the posterior spinal connector 114 or 272 or 282.

FIGS. 18-24 show an alternative embodiment of a spinal connection assembly. The spinal connection assembly 300 is similar to spinal connection assembly 100 and like reference numerals have been used to describe like components of the assemblies 100 and 300. The spinal connection assembly 300 includes a housing 302 having first and second side portions 304 and 306 and a top 308 and a bottom 310. The first side portion 304 is substantially identical to the side portion 104 described above with respect to spinal connection assembly 100 of FIGS. 1-14.

The second side portion 306 of the spinal connection assembly 300 of FIGS. 18-24 is preferably provided with a second opening 316 that is top-facing and may carry a second securement mechanism or additional securement mechanism or capture mechanism 366 for capturing a connector element, for example a rod 118. The second side portion 306, and the top-facing second opening 316 thereof, is formed by an outer wall 318 integrally connected to an inner wall 320 of the housing 302 by an arcuate bottom portion 322. The outer wall 318 and inner wall 320 each include an inner thread 324, 326 along a portion thereof, and preferably an inner thread which is positioned at the top portion 312 of the second side 306 of housing 302. The inner thread 324 of the outer wall 318 is aligned with the inner thread 326 of the inner wall 320 such that in combination the threads are adapted to receive a threaded member or capturing screw therebetween. The inner threads 324, 326 each terminate at a central portion 328 of the opening 316. The arcuate bottom portion 322 is preferably shaped to receive the rod 118, and is thus provided with a radius corresponding with the outer radius of the cylindrical rod 118 to be received therein.

Second securement mechanism 366 is provided in the top portion 312 of the second side portion 306 of the housing 302 or body. Specifically, a body screw 330 may be received within the opening. The body screw 330 preferably has a top 332 and a bottom 334, as well as a body 336 having an outer thread 338 surrounding a portion thereof which is adapted to engage the inner threads 324, 326 of the outer and inner walls 318, 320 of the second side portion 306. Preferably, the threaded body screw 330 has a length which corresponds to the length of the inner threaded portions of the walls 318, 320 in the opening 316. As a result, when the body screw 330 is in position in the second side portion 306 of the housing 302, an area 340 exists below the body screw 330 which may receive the rod 118. The body screw 330 is therefore threadably received within the top portion 312 of the housing 302, and is preferably adapted to lock the rod 118 in position in the arcuate bottom portion 322 of the opening 316. Specifically, the bottom 334 of the body screw 330 may engage the rod 118, positioned in the opening, on a surface thereof. The top 332 of the body screw 330 may include a tool engagement portion 342 for use in inserting the screw into the opening.

Assembly of the first side portion 304 of the spinal connection assembly 300 of FIGS. 18-24 may occur substantially as described for first side portion 104 described with respect to spinal connection assembly 100 in reference to FIGS. 1-14. Rod 118 may be connected to the second side portion 306 of the housing 302, and specifically within top-facing opening 316. Rod 118 is oriented generally perpendicular to the axial centerline 162 of posterior spinal connector 114 and inserted downward into the opening 316. In the opening, rod 118 rests against arcuate bottom portion 322. Then, body screw 330 is inserted by rotational insertion into the threaded portion 324, 326 of the opening. Rotation and travel of the screw continues until the bottom 334 of the screw 330 is placed in contact, and preferably in tight contact, with the rod 118, thereby retaining the rod 118 in place in the opening.

The method of use of the spinal connection assembly 300 shown in FIGS. 18-24 is substantially as described with respect to spinal connection assembly 100 shown in FIGS. 1-17. Namely, posterior spinal connector 114 is placed into the vertebra 199 by any means known in the art. Subsequently, the spinal connection assembly 300 is connected by placing the head 192 of the posterior spinal connector 114 into the bottom-facing first opening 112 in the housing 302, and locking the securement mechanism 164 over the head 192 of the posterior spinal connector 114.

As discussed above with respect to spinal connection assembly 100 and illustrated in FIGS. 15-17, more than one posterior spinal connector 114, 272, 282 may be attached to a vertebra or adjacent vertebra with spinal connection assembly 300. Namely, a first spinal connection assembly 300 may be attached to a first posterior spinal connector 114. A second spinal connection assembly 300 may be attached to the head 270 or 271 of a second posterior spinal connector 272 or 273. The first and second spinal connection assemblies may each further be interconnected by the attachment of a rod 118 which extends between the first and second spinal connection assemblies 300. In the present embodiment, a first portion 274 of the rod 118 is received by the first spinal connection assembly 300 within the opening in the second side portion 306 of the housing 302, and in particular in the top facing opening 316, and secured in place by rotational insertion of the body screw 330 to a locking or engaged position. A second portion 276 of the transverse rod 118 is received by the second spinal connection assembly within the top-facing opening in the second side portion of the housing, and secured in place by rotational insertion of the body screw to a locking or engaged position in the same manner. Cross-link 284 may also be used to connect rods 118 in adjacent assemblies, such as assemblies 300 in the same vertebra 199. It is also contemplated that alternative embodiments of spinal connection assemblies may be interconnected or locked together by the transverse member or rod 118.

FIGS. 25-31 show an alternative embodiment of the spinal connection assembly of the present invention. Spinal connection assembly 400 therein is similar to spinal connection assembly 100 and like reference numerals have been used to describe like components of assemblies 100 and 400. The spinal connection assembly 400 includes a housing 402 having first and second side portions 404, 406, interconnected by a central portion 408. The spinal connection assembly 400 also has a top 410 and a bottom 412. The first side portion 404 is substantially identical to side portion 104 described with respect to spinal connection assembly 100.

The second side portion 406 of assembly 400 is integrally connected to the first side portion 404 and a central portion 408. The second side portion 406 of the assembly is substantially similar to the first side portion 104 of spinal connection assembly 100. In this regard, the second side portion 406 includes a bottom-facing second opening 416 adapted for receiving a second connection element, and preferably a second posterior spinal connector 418. Second posterior spinal connector 418 is substantially identical to posterior spinal connector 114. The side portion 406 is preferably provided with a second opening 416 that is bottom-facing, and which may carry a second securement mechanism or additional securement mechanism or capture mechanism 466 for capturing a second connector element, such as a second posterior spinal connector 418. Similar to first side portions 104 and 404, the second side portion. 406 of the housing 402 also includes arcuate guide features or surfaces 132, 134, protrusion 144, and pin receptors 140 for receipt of pins 142. A second nut 146 is likewise received in the second side portion 406 of the housing 402.

The second securement mechanism 466 is carried by the housing 402 for capturing the second posterior spinal connector 418 within the bottom-facing second opening 416 of the second side portion 406. Securement mechanism 466 is substantially identical to securement mechanism 164 and like reference numerals have been used to describe like components of mechanisms 466 and 164. To this end, second securement mechanism 466 is received between nut 146 and first and second arcuate guide surfaces 132, 134 on the second side portion 406 of the housing, and includes first and second capture elements 168, 170 moveable on the respective first and second arcuate guide features 132, 134, spring clips 206, and limiting element 214. The second securement mechanism 466, like the first securement mechanism 164, is configured to permit the second posterior spinal connector 418 to pivot in a plane through an angle ranging from 0 to 180 degrees relative to the housing 402. More preferably, the capture elements 168, 170 are configured to permit the posterior spinal connector 418 to pivot in the plane through an angle of at least 60 degrees relative to the housing 402. In addition, the capture elements 168, 170 are configured to permit the posterior spinal connector 418 to pivot in an additional plane orthogonal to the first-named plane through an angle ranging from 0 to 120 relative to the housing 402. More preferably, the capture elements 168, 170 are configured to permit the second posterior spinal connector 418 to pivot in the additional plane through an angle of at least 60 degrees relative to the housing 402. Even more preferably, the capture elements 168, 170 are configured to permit the posterior spinal connector 418 to rotate 360 degrees about an axis extending in the first-named and additional planes.

The central portion 408 of spinal connection assembly 400 is substantially similar to second side portion 306 of spinal connection assembly 300 and like reference numbers have been used to describe like components of portions 306 and 408. In the presently described assembly 400, central portion 408 is formed of a third opening 478 which is top-facing and which may carry a third securement mechanism or additional securement mechanism or capture mechanism 480 for capturing a connector element, and specifically a rod 118. The central portion 408 and the opening 478 are formed by a first wall 482 integrally connected to a second wall 484 by an arcuate bottom portion 486. The first wall 482 and second wall 484, as well as arcuate bottom portion 486 are substantially identical to outer and inner walls 318, 320, and arcuate bottom portion 322, respectively of spinal connection assembly 300. To this end, first and second walls 482 and 484 each respectively include inner thread 324 and 326. Likewise, arcuate bottom portion 486 is provided with a radius corresponding with the outer radius of, for example, cylindrical rod 118 to be received therein and forming area 340 which may receive the rod 118.

Third securement mechanism 480 is substantially identical to that described with respect to spinal connection assembly 300, including body screw 330 which may be received by the top of the central portion 408 of the body between inner threads 324, 326. As with the previous embodiment, the body screw 330 is adapted to lock the rod 118 in position in the arcuate bottom portion 486 of the opening 478 by engaging rod 118 positioned in the opening.

Assembly of the first side portion 404 and second side portion 406 of the spinal connection assembly 400 of FIGS. 25-31 may occur substantially as described with respect to spinal connection assembly 100, and may include placing or assembling the securement mechanism 164, 466 in the opening on the side portion of the housing 402, placing a nut 146 over the opening in the side portion of the housing 402 to cover the opening and form the bottom-facing opening 112, 416, attaching the posterior spinal connector 114, 418 by inserting the connector element into the bottom-facing opening between the capture elements 168 and 170 and inserting a capture screw 214 into the aperture 158 in the nut within the top portion of the housing 402 to engage the capture elements with the anterior portion 224 of the capture screw 214. As discussed, this results in causing the top portions 174 of each of the capture elements to move apart through travel along the arcuate guide features 132 and 134 which moves the lower portion 176 of the capture elements downward and inward beyond the equator of the spherical head of the posterior spinal connector 114, 418, thereby engaging the lower portion of the spherical head. Travel continues until the capture screws contact the heads of the posterior spinal connectors, restricting axial travel and securing the posterior spinal connector(s) to the housing 402.

A connector element, such as rod 118, may be connected to the central portion 408 of the housing 402 having top-facing third opening 478 substantially as described with respect to securement of rod 118 in the top-facing second opening 316 in spinal connection assembly 300. The rod 118 is inserted generally perpendicular to the axial centerline 162 of the posterior spinal connector 114 or 418 and downward into the opening, such that it rests against the arcuate bottom portion 486. Body screw 330 is inserted into the inner thread 324, 326 of the opening 478. Rotation and travel of the screw continues until the bottom of the screw is placed in contact, and preferably, tight contact, with the rod 118, thereby retaining the rod 118 in place in the opening.

The method of use of the spinal connection assembly 400 shown in FIGS. 25-31 is substantially as described with respect to spinal connection assembly 100 shown in FIGS. 15-17. Namely, the posterior spinal connector 114, or first posterior spinal connector 114 is placed into the vertebra or adjacent vertebra by any means known in the art. Second posterior spinal connector 418 may also be attached or placed into vertebra by any known means. Subsequently, the spinal connection assembly 400 is connected as described, by placing the head 192 of the first posterior spinal connector 114 into the bottom-facing first opening 114 in the first side portion 404 of the housing 402, placing the head 192 of the second posterior spinal connector 418 into the bottom-facing second opening 416 in the second side portion 406 of the housing 402, locking the first securement mechanism 164 over the head 192 of the first posterior spinal connector 114, and locking the second securement mechanism 466 over the head 494 of the second posterior spinal connector 418.

As discussed above with respect to spinal connection assembly 100 and illustrated in FIGS. 15-17, more than one posterior spinal connector 114, 272, 282 may be attached to a vertebra 199 or adjacent vertebra 278, 280 with spinal connection assembly 400. Adjacent vertebra 199, 278, 280 may be attached by a plurality of spinal connection assemblies 400, substantially as shown and described with respect to spinal connection assembly 100 shown in FIGS. 16-17. For example, a first spinal connection assembly 400 may be attached to a first posterior spinal connector 114 and second posterior spinal connector 418 in the manner described herein. A second spinal connection assembly may be attached to the head of a third posterior spinal connector, and where applicable, a fourth posterior spinal connector in the same manner. The first and second spinal connection assemblies may each further be interconnected by the attachment of a connector element, such as rod 118, which extends between the first spinal connection assembly 400 and a second spinal connection assembly. In the presently described embodiment, a first portion of the rod 118 is received by the first spinal connection assembly within the top-facing third opening 478 in the central portion of the housing, and secured in place by rotational insertion of the body screw 330 or third securement mechanism or additional securement mechanism or capture mechanism 466 to a locking position. A second portion of the transverse rod 118 is received by the second spinal connection assembly 400 within the top-facing third opening 478 in the center portion of the housing, and secured in place by the body screw 330 in the same manner. Adjacent assemblies 400 may be interconnected in a single vertebra 199 by a cross-link or similar device as discussed with respect to assembly 100 shown in FIG. 15. As one example, the width of assembly 400 may be varied to interconnect with an adjacent assembly in a single vertebra. It is also contemplated that alternative embodiments of spinal connection assemblies may be interconnected or locked together by the transverse member or rod 118.

FIGS. 32-40 show an alternative embodiment of a spinal connection assembly of the present invention. The spinal connection assembly 500 therein is similar to spinal connection assembly 100 and like reference numerals have been used to describe like components of the assemblies. The spinal connection assembly 500 includes a housing 502 having first and second side portions 504, 506, and a top 508 and a bottom 510. The first side portion 504 is substantially identical to the first side portion 104 described with respect to spinal connection assembly 100.

The second side portion 506 is substantially similar to the first side portion 104 as well except that the second side portion 506 is configured to receive a second connection element in the form of a rod 118, and preferably a cylindrical rod. The second side portion 506 has a bottom-facing second opening 516 and includes second securement mechanism or additional securement mechanism or capture mechanism 566 for capturing the rod 118 within the second opening 516, including third and fourth capture elements 518, 520 and spring clips 206, pins 142 and pin receptors 140, as well as a second limiting element 214 received within a second nut 146 and aligned with a central axis 266 of the connection element for restricting travel of the second connection element, in this case the rod 118, within the housing 502. The second side portion 506 of the housing 502 further includes arcuate guide features 132, 134. Third and fourth capture elements 518, 520 are disposed in spaced-apart positions within the second opening 516 and moveable on the respective arcuate guide features 132, 134 in a manner substantially identical to assembly 100, shown in FIGS. 2a & b and FIGS. 3a & b, from an opened first position for receiving the rod 118 and a second position for capturing the rod 118.

Figure 39:
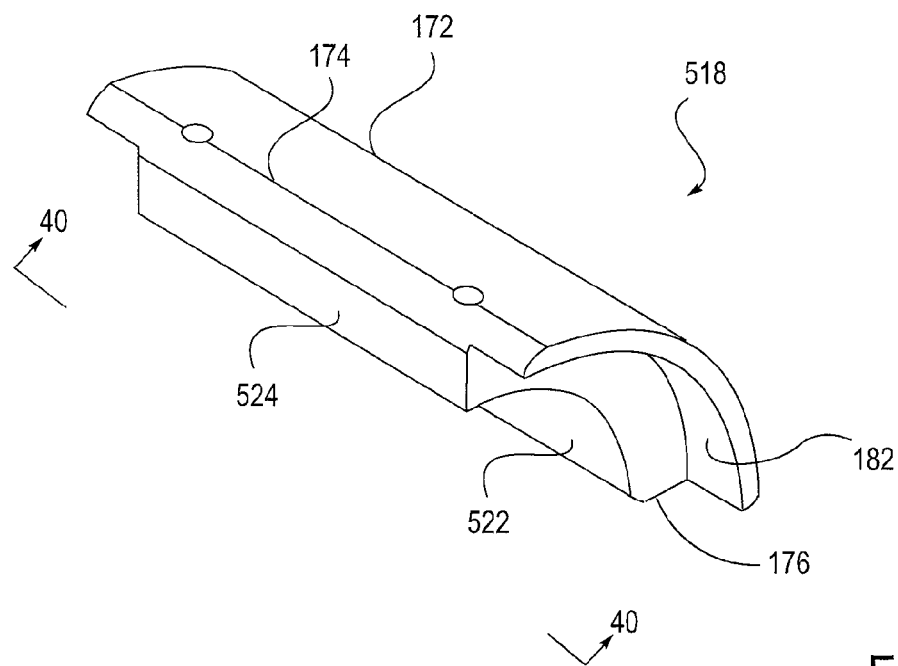
FIG. 39 is a perspective view of a capture element for use with the spinal connection assembly of FIG. 32, taken from line 39-39 of FIG. 36, having an inner arcuate surface.
Figure 40:
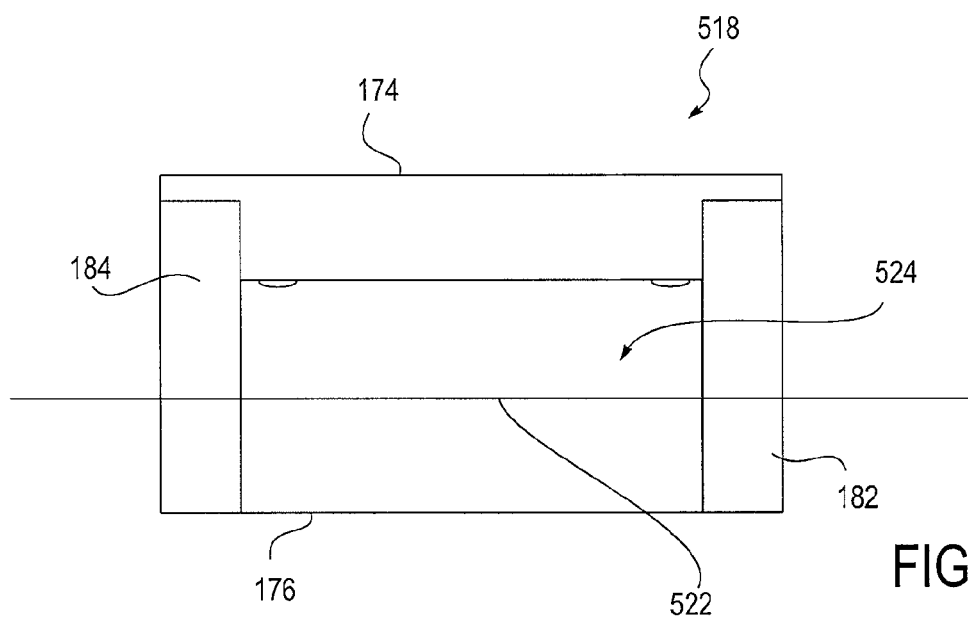
FIG. 40 is an elevational view of a capture element for use with the spinal connection assembly of FIG. 32, taken from line 40-40 of FIG. 39.

Third and fourth capture elements 518, 520 are substantially similar to first and second capture elements 168, 170, except that third and fourth capture elements 518, 520 have an inner arcuate surface 522 formed to engage and move along a cylindrical rod 118 (see FIGS. 39-40). The inner arcuate surface 522 is formed from, or on, the securement portion 524 of the capture element. The capture elements, similar to capture elements 168, 170, also include outer arcuate surface 172, top portion 174, lower portion 176, and guide surfaces 182, 184.

Assembly of the second side portion 506 of the spinal connection assembly 500 of FIGS. 32-40 may occur substantially identical to that described with respect to spinal connection assembly 100. Likewise, posterior spinal connector 114 may be captured by first side portion 504 substantially identical to that described with respect to spinal connection assembly 100. Rod 118 may be connected to the second side portion 506 of the housing 502 substantially similar to the capture of the posterior spinal connector 114 in the first side portion 104 as well. For example, rod 118 is attached by inserting the rod 118 generally perpendicular to the axial centerline 162 of the posterior spinal connector 114 into the bottom-facing second opening 516 of the second side portion 506 of the housing 502 between the third and fourth capture elements 518, 520. A capture screw 214 is inserted into the aperture in the top portion or nut 146 in the housing 502 to engage the capture elements 518, 520 with the anterior portion 226 of the capture screw 214, thereby causing the separation of the top portions 174 of each of the capture elements 518, 520 and forcing the capture elements 518, 520 to travel along the arcuate guide features 132, 134 on the second side portion 506 of housing 502. The lower portion 176 of the capture elements move downward and inward beyond the axial centerline 266 of the cylindrical rod 118, thereby engaging a lower portion of the cylindrical rod 118. Travel continues until the capture screw 214 contacts the rod 118, forming a friction fit therewith. The rod 118 is secured in place in the second opening 516 by both the second capture screw 214 and the third and fourth capture elements 518, 520.

The method of use of the spinal connection assembly 500 shown in FIGS. 32-40 is substantially as described with respect to spinal connection assembly 100 and shown in FIGS. 15-17. Namely, the posterior spinal connector 114 is placed into the vertebra by any means known in the art, the spinal connection assembly 500 is connected by capture of the head 192 of posterior spinal connector 114 in bottom-facing first opening 112 in the first side portion 104 of the housing 502, and locking the first securement mechanism 164 over the head 192 of the first posterior spinal connector 114. Similarly, a plurality of posterior spinal connectors 114, may be attached to a vertebra (FIG. 15) or adjacent vertebra (FIG. 16-17) substantially as described with respect to spinal connection assembly 100. To this end, a first spinal connection assembly 500 may be attached to a first posterior spinal connector 114 in the manner described herein. A second spinal connection assembly may be attached to the head of a second posterior spinal connector in the manner described herein. The first and second spinal connection assemblies may each further be interconnected, which may occur by the attachment of a connector element, such as rod 118, which rod is captured by assembly 500 as described herein and extends between the first spinal connection assembly 500 and the second spinal connection assembly. Adjacent vertebra 199, 278, 280 may be attached by a plurality of spinal connection assemblies substantially as described with respect to spinal connection assembly 100 and shown in FIGS. 16-17. It is also contemplated that alternative embodiments of spinal connection assemblies may be interconnected or locked together.

Figure 43:
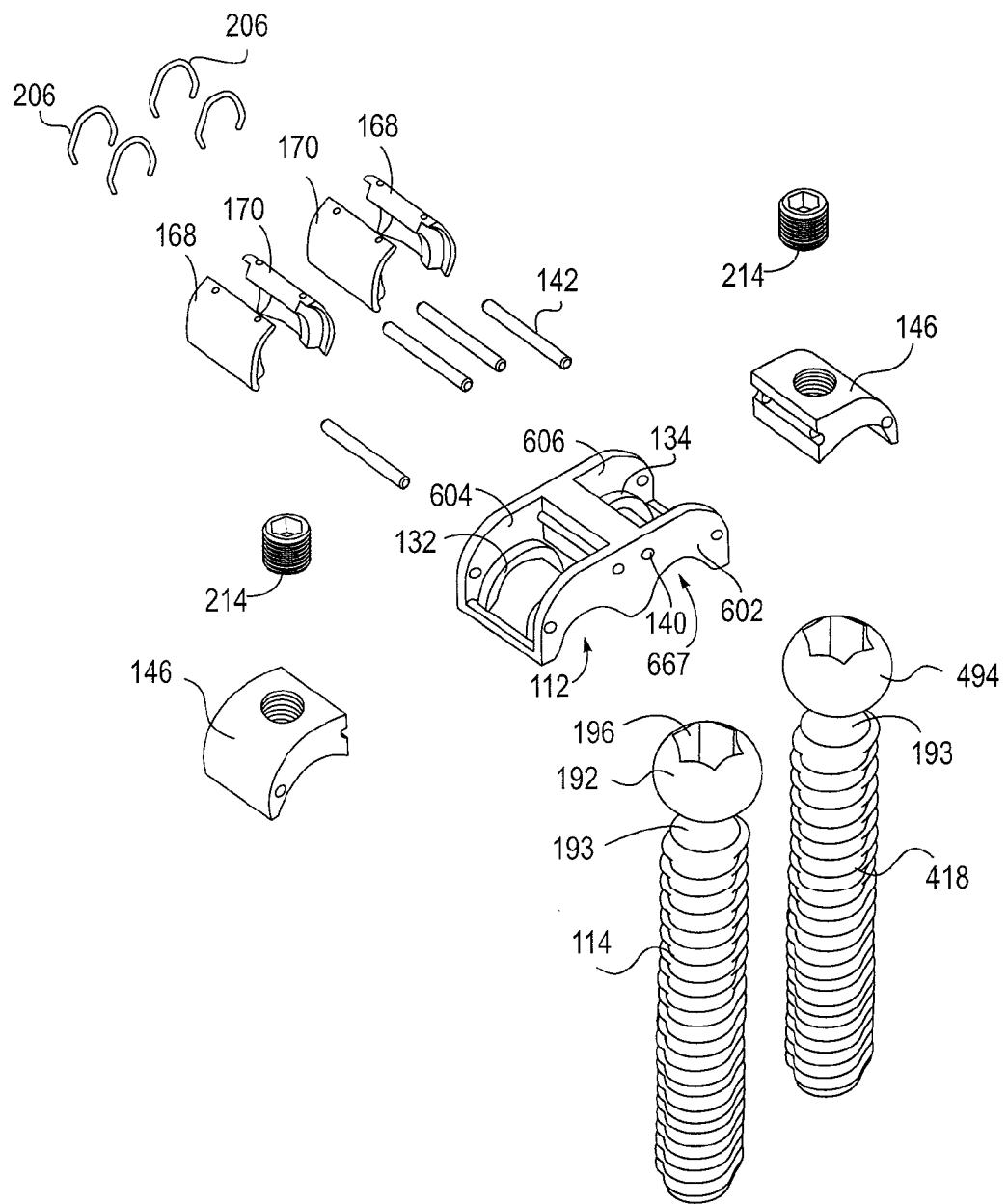
FIG. 43 is an exploded view of the spinal connection assembly of FIG. 41.
Figure 44:
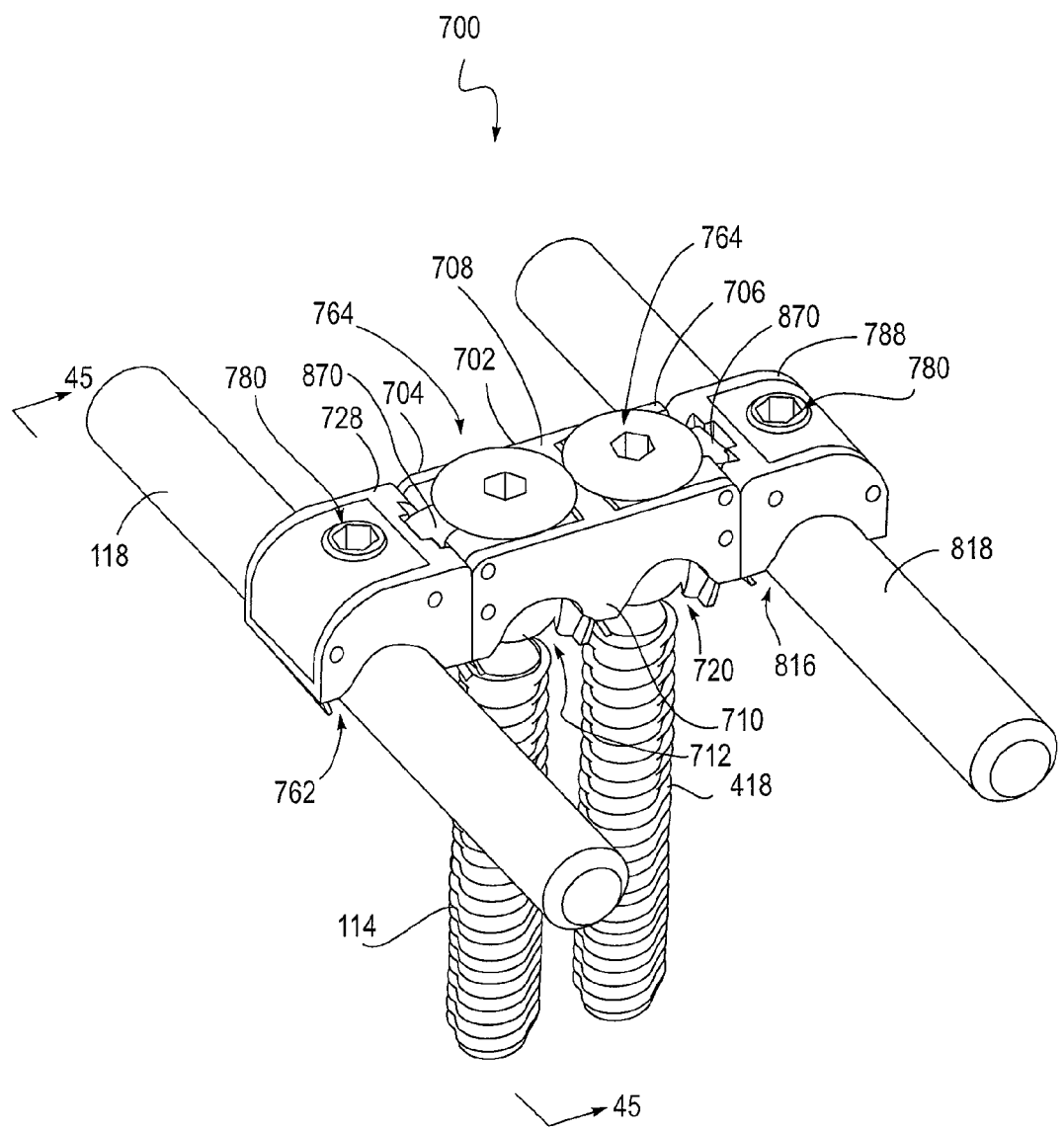
FIG. 44 is a perspective view of an alternative embodiment of the spinal connection assembly of the present invention, having a second bottom-facing opening and first and second side housings, together with two posterior spinal connector and two rods.
Figure 45:
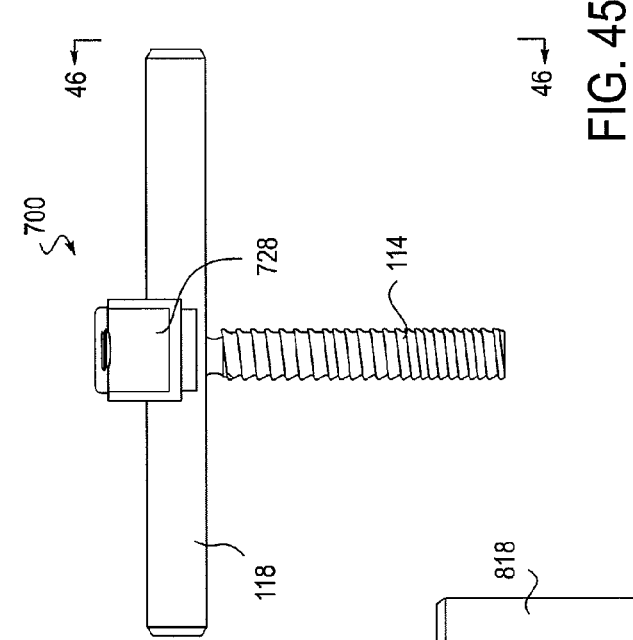
FIG. 45 is an elevational view of the spinal connection assembly of FIG. 44, taken from line 45-45 of FIG. 44.
Figure 47:
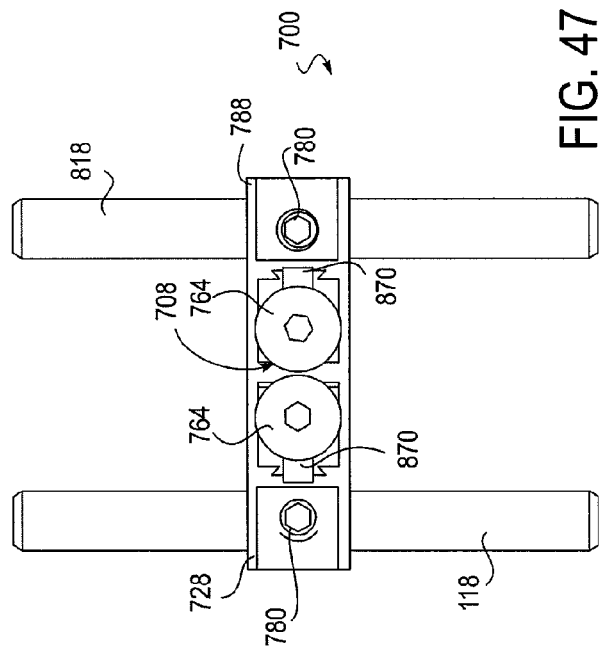
FIG. 47 is a plan view of the spinal connection assembly of FIG. 44, taken from line 47-47 of FIG. 46.
Figure 46:
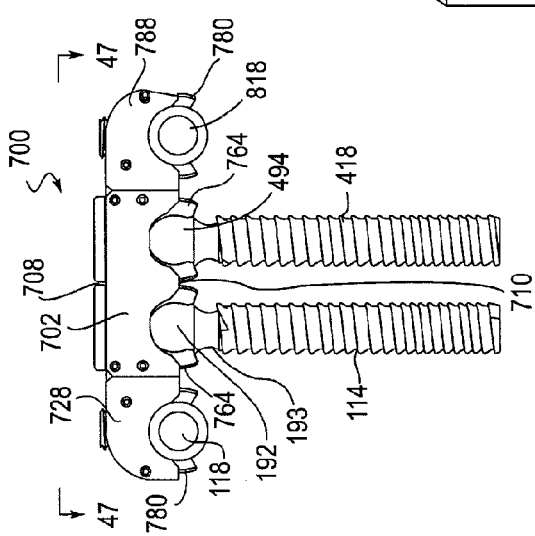
FIG. 46 is an elevational view of the spinal connection assembly of FIG. 44, taken from line 46-46 of FIG. 45.
Figure 48:
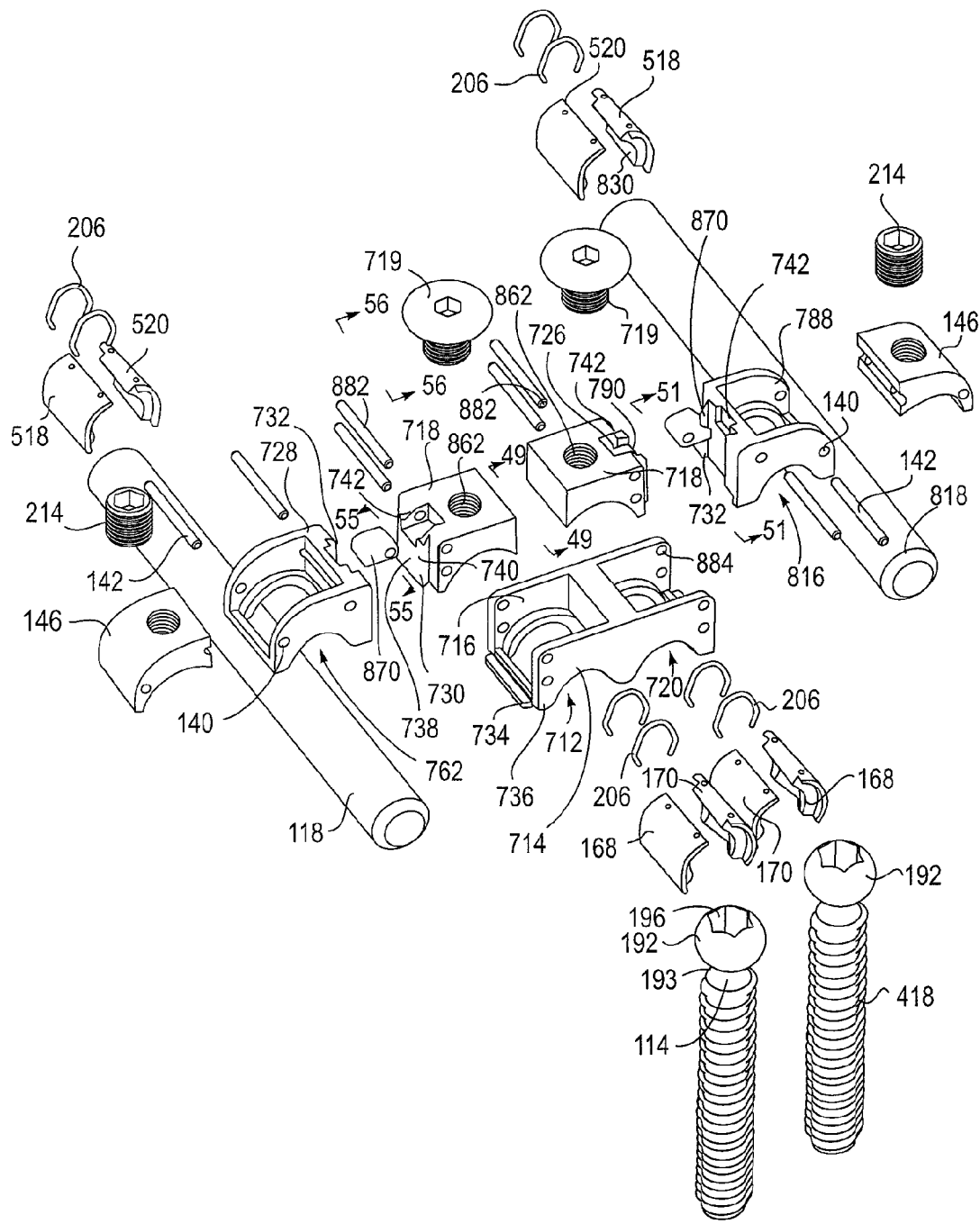
FIG. 48 is an exploded view of the spinal connection assembly of FIG. 44.

FIGS. 41-43 show an alternative embodiment of a spinal connection assembly of the present invention. The spinal connection assembly 600 therein is similar to spinal connection assembly 100 and like reference numerals have been used to describe like components of the assemblies. The spinal connection assembly 600 includes a housing 602 having first and second side portions 604, 606, and a top 608 and a bottom 610. Housing 602 is substantially identical to housing 502 as described with respect to spinal connection assembly 500. First side portion 604 and second side portion 606 are each substantially identical to side portion 104 described with respect to spinal connection assembly 100. To this end, first and second side portions 604, 606 each may include a bottom-facing opening 112, 667 adapted for receiving a posterior spinal connector 114, 418, a securement mechanism 164 including capture elements 168, 170 moveable on arcuate guide surfaces 132, 134, and spring clips 206, as well as a limiting element 214 received within a nut 146. Pins 142 and pin receptors 140 may also be provided for attachment of the nut 142 as described for spinal connection assembly 100.

Assembly of the first and second side portions 604, 606 of the spinal connection assembly 600 shown in FIGS. 41-43 may occur substantially identical to that described with respect to the assembly of the first side portion 104 as described with respect to spinal connection assembly 100.

The method of use of the spinal connection assembly 600 shown in FIGS. 41-43 is substantially similar to the spinal connection assembly 100 described with respect to spinal connection assembly 100 and shown in FIGS. 15-17, except that a rod 118 is not connected to assembly 600. Accordingly, a first posterior spinal connector 114 is placed into the vertebra by any means known in the art. A second posterior spinal connector 418 may also be attached or placed into the vertebra by any known means. Subsequently, the spinal connection assembly 600 is connected by placing the head 192 of each posterior spinal connector 114, 418 into the downward-facing opening 112, 667 in the housing 602, and locking the securement mechanisms 164 over the head 192 of the posterior spinal connectors 114, 418.

FIGS. 44-56 show an alternative embodiment of the spinal connection assembly of the present invention. The spinal connection assembly 700 therein is similar to spinal connection assembly 100 and like reference numerals have been used to describe like components of the assemblies. Spinal connection assembly 700 includes a housing 702 having first and second side portions 704, 706, and a top 708 and a bottom 710. The first side portion 704 and second side portion 706 are substantially similar to first side portion 104 described with respect to spinal connection assembly 100. However, first and second side portions 704, 706 of housing 702 include first and second sidewalls 714, 716 which are formed, in the preferred embodiment, by substantially squared or rectangular portions, and include a corresponding shaped nut 718. The first and second side portions 704, 706 also each include securement mechanisms or capture mechanisms 764 for capturing a connector element or posterior spinal connector 114, 418 within the first opening 712 and second opening 720 which may be provided in the first and second portions 704, 706, including first and second capture elements 168, 170, and spring clips 206. A limiting element 719 is received within nut 718 and aligned with a central axis 162 of the posterior spinal connector 114 or 418 for restricting axial travel of the posterior spinal connector within the housing 702. Pin receptors 884 and pins 882 are also provided for securing nut 718 in place on the housing 702 substantially as described for pin receptors 140 and pins 142 of spinal connection assembly 100.

Figure 49:
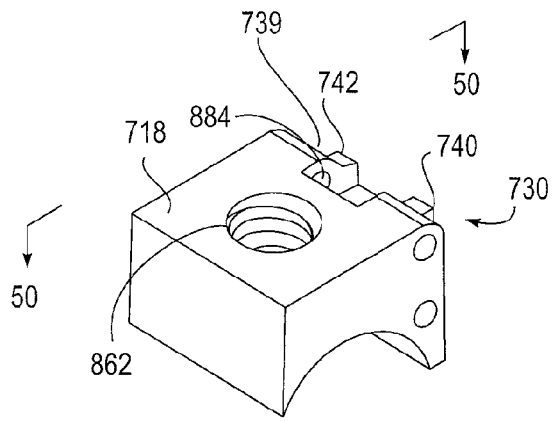
FIG. 49 is perspective view of a nut in the spinal connection assembly of FIG. 44, taken from line 49-49 of FIG. 48.
Figure 50:
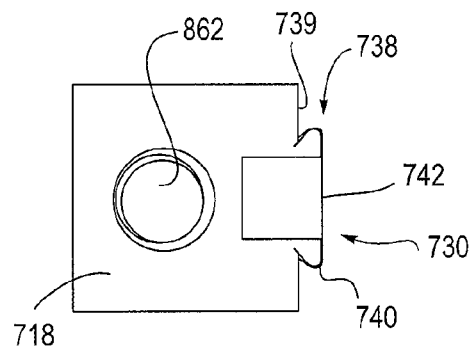
FIG. 50 is a plan view of the nut of the spinal connection assembly shown in FIG. 44, taken from line 50-50 of FIG. 48.
Figure 51:
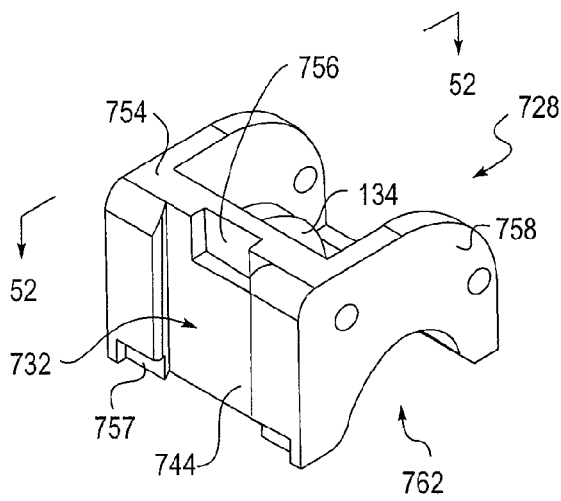
FIG. 51 is a perspective view of a side housing of the spinal connection assembly shown in FIG. 44, taken from line 51-51 of FIG. 48.
Figure 52:
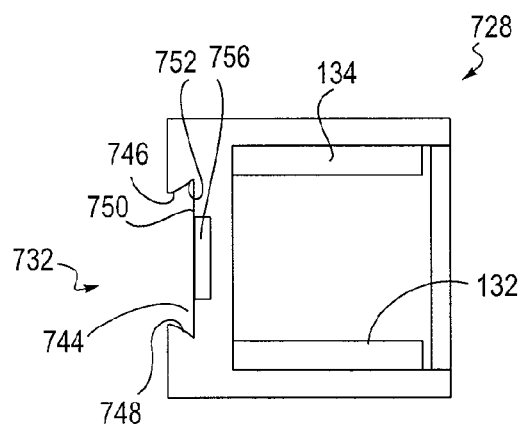
FIG. 52 is a plan view of the side housing of the spinal connection assembly shown in FIG. 44, taken from line 52-52 of FIG. 51.

The spinal connection assembly 700 shown in FIGS. 43-56 further includes a first side housing 728 and cooperative attachment elements 730 or 732 carried by the first side portion 704 of the housing 702 and the first side housing 728 for removably securing the first side housing 728 alongside the first side portion 704. The first side portion 704 of the housing 702 is provided with a flange 734 which extends outward from the bottom 736 of the first side portion 704. As can be seen in FIGS. 49-50, the cooperative attachment element 730 of the first side portion 704 is positioned on the nut 718, and preferably includes an outwardly extending protrusion 738 on the nut, and preferably end wall 739 of the nut 718. The outwardly extending protrusion 738 may include a wider portion 740 so as to be keyed with a correspondingly shaped recess and to resist pullout of the cooperative attachment element. Preferably, the flange 734 (see FIG. 48) of the housing 702 extends a distance corresponding to or greater than the outwardly extending protrusion 730. The protrusion 730 and nut 718 further include a downwardly extending recess 742 on the upper portion thereof. As can be seen in FIGS. 51-52, the cooperative attachment element 732 of the first side housing 728 is formed of a slot or recess 744 adapted to receive the outwardly extending protrusion 738. More specifically, the recess 744 is shaped to correspond with the shape of the outwardly extending protrusion and has a first side-wall 746, second side wall 748, and a third wall 750 interconnecting the first and second side walls 746, 748. The recess 744 preferably has a wider interior portion 752 so as to be keyed with the outwardly extending protrusion 738 and cooperatively resist pullout. The cooperative attachment elements 730, 732 thus form a tongue and groove arrangement.

A transverse recess 757 corresponding to the flange 734 of housing 702 is also provided on a lower portion of the first side housing 728. The top portion 754 of the first side housing 728 and recess 744 include a downwardly extending recess 756 corresponding with the downwardly extending recess 742 of the nut 718 carried by first side portion 704.

The first side housing 728 is also substantially similar to second side portion 506 of spinal connection assembly 500, including bottom-facing opening 762, or third opening, for receiving a connector element, such as a rod 118, arcuate portions 132, 134, capture elements 518, 520, spring clips 206, nut 146, and capture screw 214. Pins 142 and pin receptors 140 may also be provided for attachment of nut 146. The third securement mechanism or additional securement mechanism or capture mechanism 780 is substantially identical to securement mechanism formed by capture elements 518, 520 carried by arcuate portions 132, 134, spring clips 206 and capture screw 214 as described for spinal connection assembly 500. The third securement mechanism 780 is carried by the side housing for capturing the rod 118 within the bottom-facing third opening 762 of the first side housing 728.

The second side portion 706 of the housing 702 also preferably includes a second side housing 788 which is substantially identical to the first side housing 728 of spinal connection assembly 700. In this regard, second side housing 788 includes cooperative attachment element 730 or 732, as well as a fourth securement mechanism or further additional securement mechanism or capture mechanism 780 that captures rod 818 in a fourth downward facing opening 816.

Figure 53:
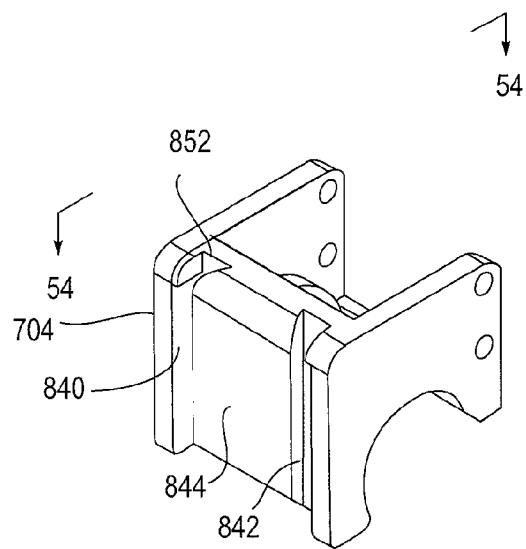
FIG. 53 is a perspective view of an alternative embodiment of a side housing of the spinal connection assembly of FIG. 44.
Figure 54:
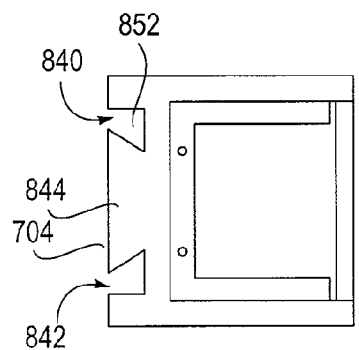
FIG. 54 is a plan view of the side housing of the spinal connection assembly of FIG. 44, taken from line 54-54 of FIG. 53.
Figure 55:
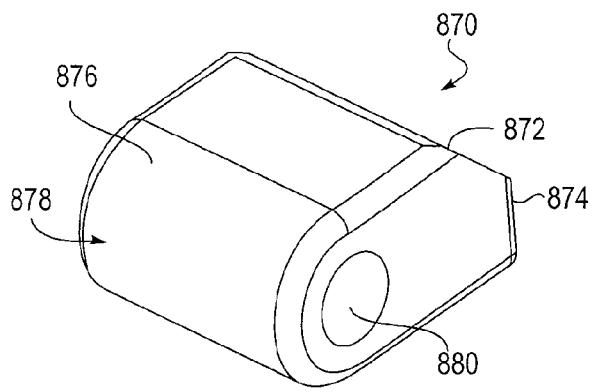
FIG. 55 is an elevational view of a locking member in the spinal connection assembly of FIG. 44, taken from line 55-55 of FIG. 48.
Figure 56:
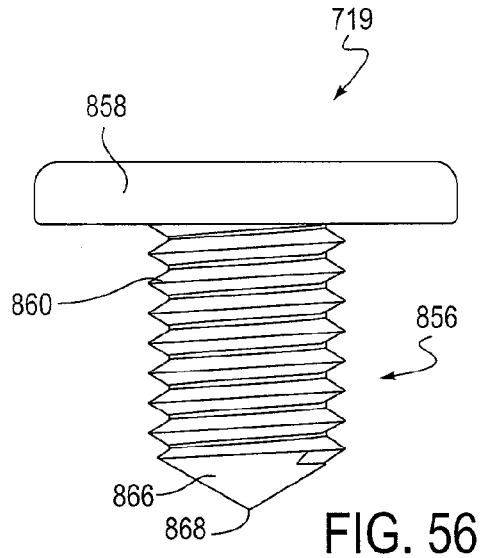
FIG. 56 is an elevational view of a capture screw in the spinal connection assembly of FIG. 44, taken from line 56-56 of FIG. 48.
Figure 57:
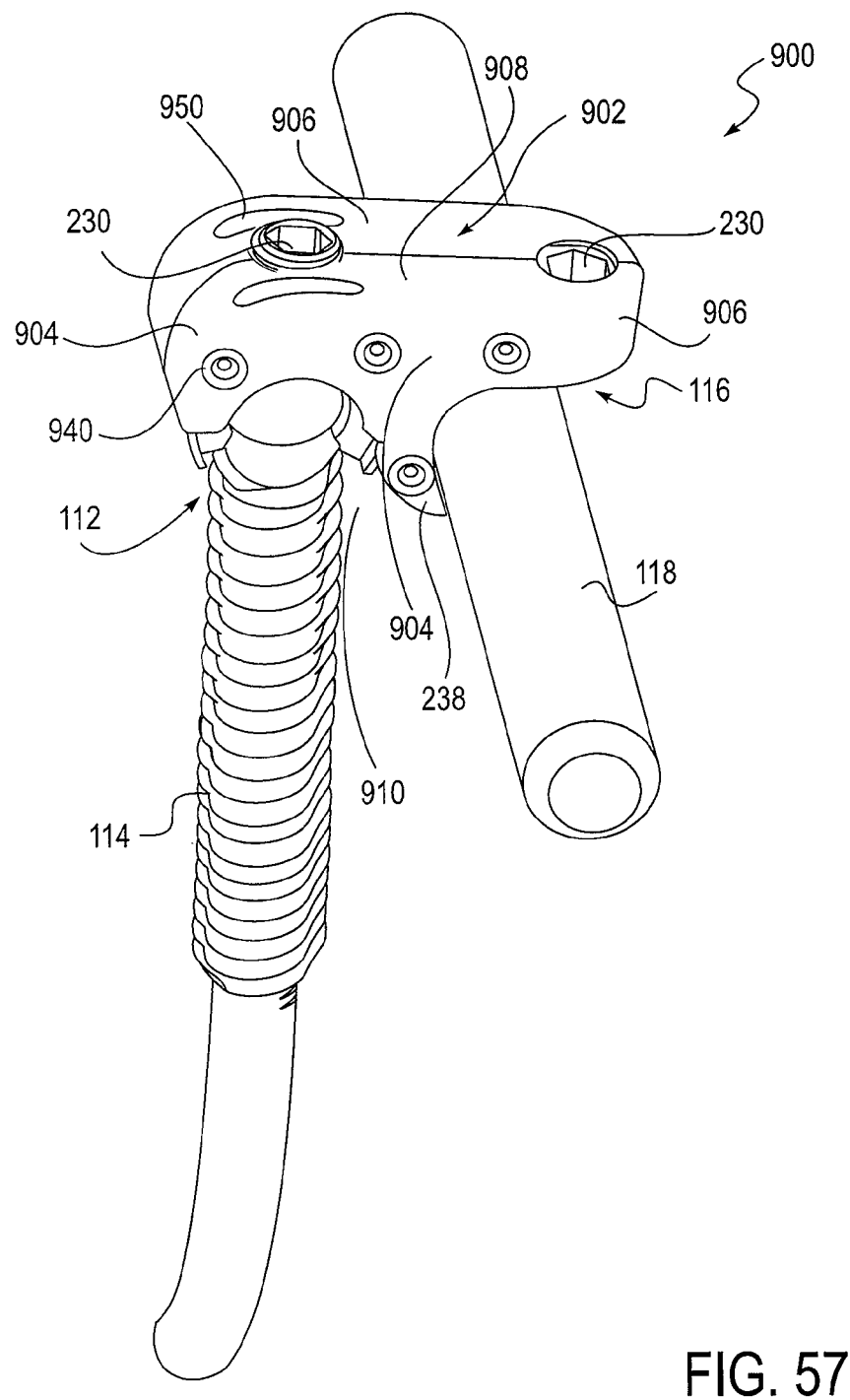
FIG. 57 is a perspective view of an alternative embodiment of the spinal connection assembly of the present invention, including a separable housing having a side-facing second opening, together with a posterior spinal connector and a rod.
Figure 58:
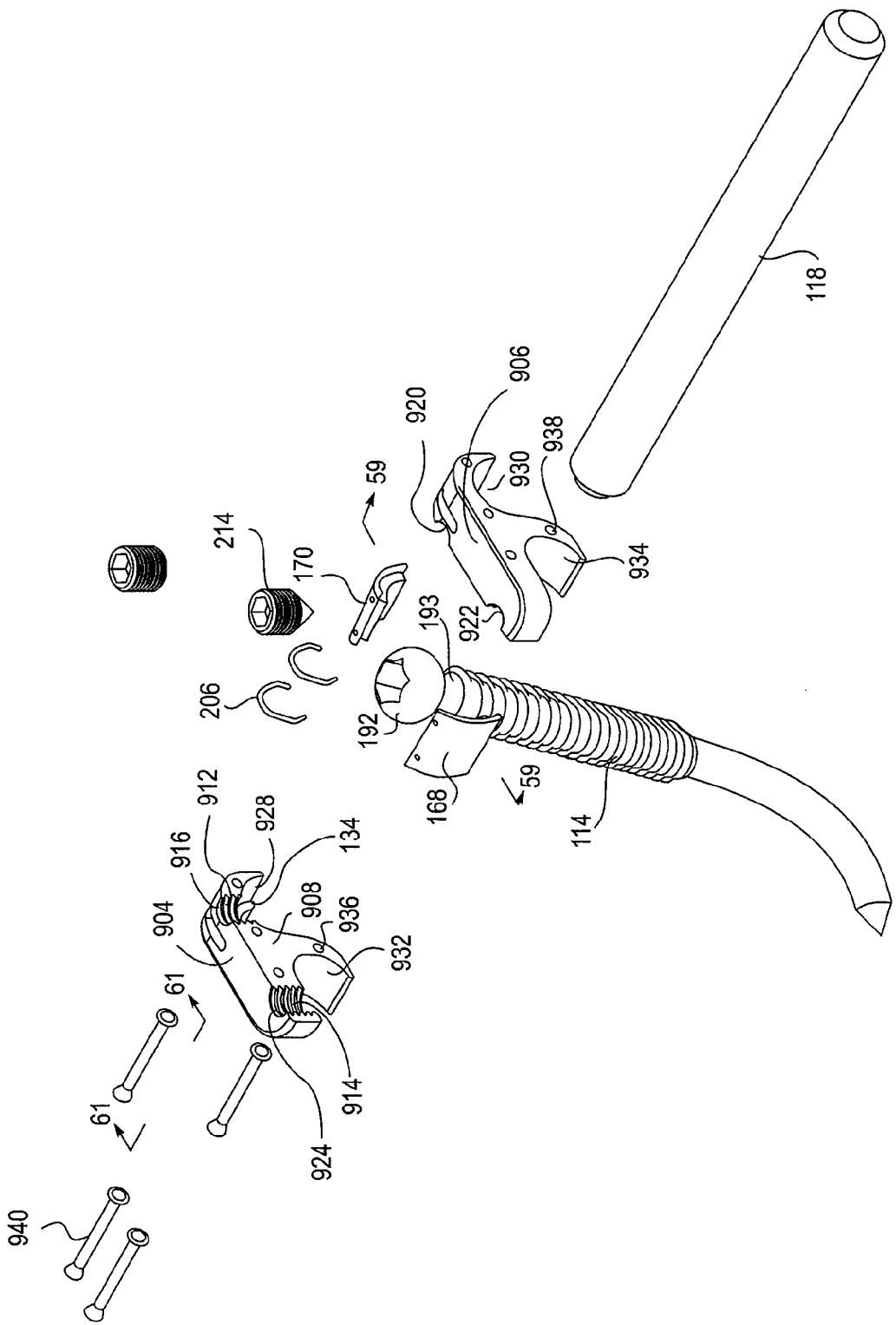
FIG. 58 is an exploded view of the spinal connection assembly of FIG. 57.
Figure 59:
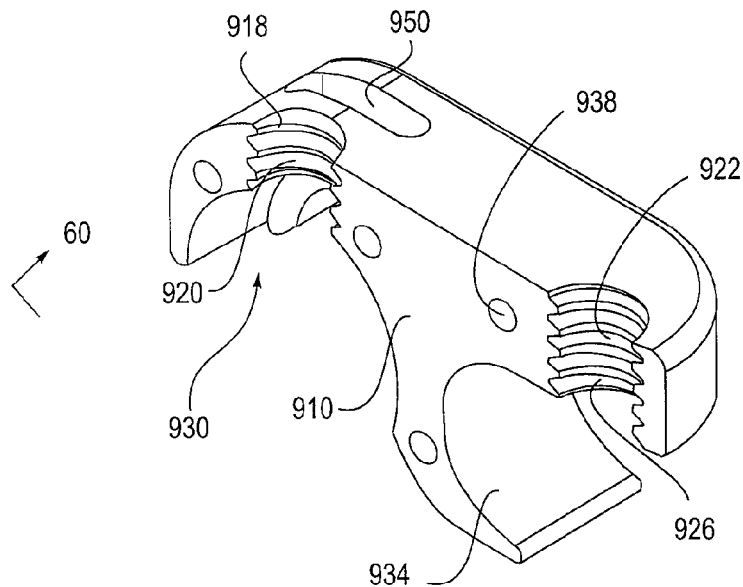
FIG. 59 is a perspective view of a side member of the housing of the spinal connection assembly shown in FIG. 57, taken from line 59-59 of FIG. 58.
Figure 60:
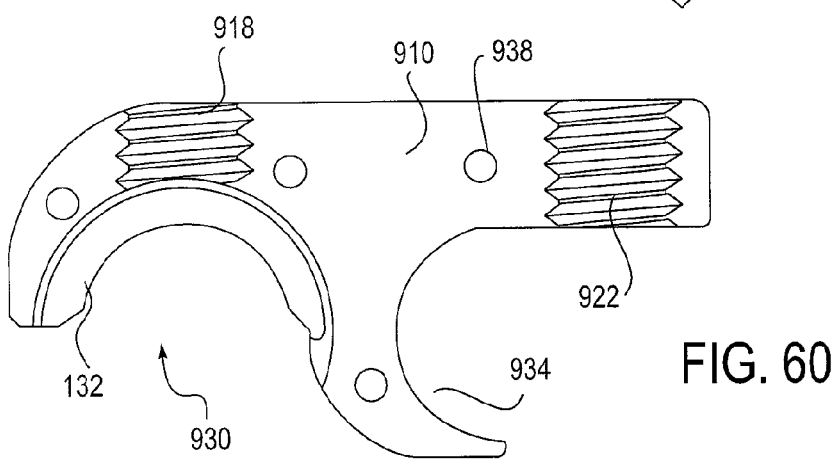
FIG. 60 is an elevational view of the side member of the housing of the spinal connection assembly shown in FIG. 59, taken from line 60-60 of FIG. 59.
Figure 61:
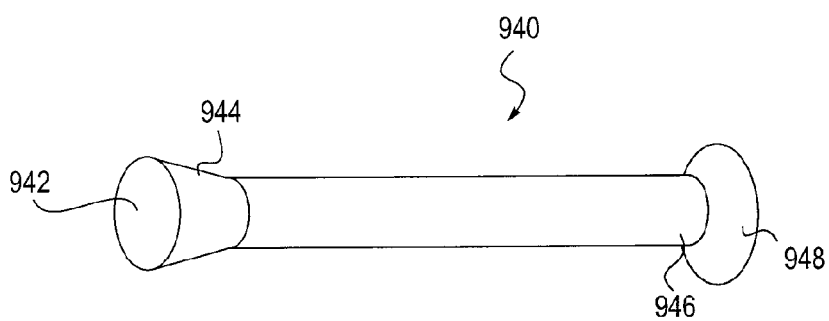
FIG. 61 is a perspective view of a pin and cap assembly in the spinal connection assembly of FIG. 57, taken from line 61-61 of FIG. 58.

Alternative cooperative attachment elements are shown in FIGS. 53-54, and may include first and second recesses 840, 842, or plurality of recesses on a side surface 844 of the side portion 704 or 706 and first and second protrusions 846, 848 or a plurality of protrusions on a side surface of the side housing (not shown), forming a tongue and groove or key-type arrangement. The recesses 840, 842 and corresponding protrusions may be irregular shaped so as to include a wider portion 852 of the to resist pull-out of the tongue from the groove. It is appreciated that the protrusions, or tongue, and groove, or recess, may be respectively positioned on opposite or surfaces from that described without departing from the overall scope of the present invention The limiting elements, and specifically first and second capture screws 719 of the presently described embodiment are preferably formed of an anterior threaded portion 856 and a posterior head 858 which has an outer diameter greater than that of the anterior threaded portion, and more preferably, greater than that of the nut 718, such that it engages the top portion 708 of the housing 702. The outer thread 860 on the threaded portion 856 has a pitch which is adapted to mate with the inner thread in the nut aperture 862. Preferably, the anterior portion 856 of the limiting element also includes a portion which may engage the capture elements such as an inwardly tapered or conical portion 866 terminating in a tip 868.

A locking element 870 is also provided in the top recesses of each of the first and second side portions 704, 706 and first and second side housings 728, 788. Locking element 870 includes an angled surface 872 on a first end 874 and an outer arcuate surface 876 on a second end 878. An aperture 880 extends through the locking element. Locking element(s) 870 are held in place by at least one pin 882 inserted into the aperture, which pin is also received by an aperture 884 in the housing, and may be pivotable about the pin.

Assembly of the first and second side portions 704, 706 of the housing 702 for spinal connection assembly 700 of FIGS. 44-56 may occur substantially as described with respect to the assembly of the first side portion 104 of spinal connection assembly 100, and to this end may include placing or assembling the securement mechanism or capture mechanism 764 in the side portion 704, 706 of the housing 702 and attaching the posterior spinal connector 114 or 418 by inserting the connector element into the bottom-facing opening 712, 720 of the side portion of the housing between the capture elements 168, 170 and inserting the capture screw 719 into the aperture 862 in the nut 718, to engage the capture elements with the conical portion 866 of the capture screw, thereby causing movement of each of the capture elements so as to travel along the arcuate guide features on the housing 702, capturing the spherical head 192 of the posterior spinal connector 114, 418.

The first and second side housings 728, 788 are attached to the respective side portion 704, 706 of the housing 702 in the same manner. The first cooperative attachment element 730 positioned on the side housing is placed in cooperative, but removable engagement with the second cooperative attachment element 732 positioned on the side portion of the housing. Preferably, the cooperative attachment elements are engaged by sliding the first element 730 over the second element 732. More specifically, the side housing 728, 788 is slid from the top 708 of the housing downward over the cooperative attachment element 732. The housing 702 may be further locked between the side portion of the housing and the side housing by locking arm 870. Specifically, locking arm or element 870 is inserted into the top downward-facing recess 756 formed in each of the side portion and side housing. Locking arm 870 is then secured in place by insertion of pin 882 through the aperture 884 in the side walls of the side portion of the housing and through a corresponding aperture 880 in the locking element. The locking element 870 cooperates with the flange 734 or 794 extending from the bottom portion of the side housing to retain the side housing in position on the side portion. Locking element 870 may alternatively be pre-installed on the nut or housing and pivoted to an open or unlocked position. Then, following attachment of the side housing, the locking element may be locked by pivoting the element into the recess formed by the side portion with attached side housing. First and second rods 118, 818 may then be attached to the first side housing 728 and second side housing 788 by insertion into the bottom facing third and fourth openings substantially as described with respect to the installment of rod 118 in the bottom-facing opening 516 on second side portion 506 of spinal connection assembly 500.

The method of use of the spinal connection assembly 700 shown in FIGS. 44-56 is substantially similar to spinal connection assembly 100 shown in FIGS. 15-17. Namely, the posterior spinal connector 114, or first posterior spinal connector 114 is placed into the vertebra by any means known in the art. A second posterior spinal connector 418 may also be attached or placed into the vertebra by any known means. Subsequently, the spinal connection assembly 700 is connected as described, by placing the head 192 of the posterior spinal connector 114 or 418 into the bottom-facing opening 712, 720 in the first side portion 704 and second side portion 706 of the housing 702, and locking the first securement mechanism 764 over the head 192.

First and second rods 118, 818 may also be connected to the assembly by use of the third and fourth securement mechanisms or additional securement mechanisms or capture mechanisms 780 in a manner substantially identical to that described with respect to the assembly of spinal connection assembly 500. In particular, the third and fourth securement mechanisms 780, carried by the first side housing 728 and second side housing 788, receive and secure first and second rods 118, 818 in the manner described with respect to rod 118 as secured by spinal connection assembly 500. Additional spinal connection assemblies may be connected to the rod or rods in the same manner on either side of the assembly as described herein with respect to previous embodiments. It is also contemplated that alternative embodiments of spinal connection assemblies may be interconnected or locked together by the transverse member or rod. For example, one or more spinal connection assemblies 700 may be connected on adjacent vertebra 199, 278, 280 as described with respect to previously described spinal connection assemblies. Adjacent assemblies 700 on the same vertebra 199 may also be connected as described with respect to spinal connection assembly 100 in reference to FIG. 15.

FIGS. 57-61 show an alternative embodiment of the spinal connection assembly of the present invention. The spinal connection assembly 900 therein is substantially similar to spinal connection assembly 100 and like reference numerals have been used to describe like components of the assemblies. Spinal connection assembly 900 includes a housing 902 having first and second side portions 904, 906 and a top 908, and a bottom 910. First side portion 904 and second side portion 906 are each substantially identical to the respective first side portion 104 and second side portion 106 described with respect to spinal connection assembly 100, except that first side portion 904 does not include nut 146.

Additionally, housing 902 of spinal connection assembly 900 as shown in FIGS. 57-61, is formed from more than one member, and preferably a plurality of members. In the illustrated embodiment, two members, namely left and right separable members 905, 907 or sections form the housing 902. Each of the left and right members 905, 907 forms a portion of the housing 902 and include a sidewall 908, 910 having a recess 912, 914 with an inner thread 916, 918 in the first side portion 904 of the sidewall and a recess 920, 922 with an inner thread 924, 926 in the second side portion 106 of the sidewall. The threaded recesses are formed in the sidewalls of the left and right sections so as to create a minor image. Thus, each recess is adapted to form threaded aperture 148 and 242 with the corresponding recess in the opposing member. Each of the left and right separable members 905, 907 or sections also include a portion of the bottom-facing first opening 112. The portion 928, 930 of the bottom-facing first opening includes an arcuate guide member 132 or 134 thereon for operable engagement with the corresponding capture element. Additionally, each of the left and right separable members 905, 907 or sections include an arcuate portion 932, 934 forming the side-facing second opening 116.

The left and right separable members 905, 907 each include at least one, and preferably more than one pin receptor 936, 938 extending laterally therethrough. The pin receptors are aligned with the pin receptors on the corresponding left or right side section of the housing 902. A pin, or securement pin 940, is received within the combined pin receptors 936, 938 when the sidewalls 908, 910 are in contact. The securement pin 940 includes a first end 942 having an outwardly tapered or conical portion 944 and a second end 946 carrying a cap 948, and preferably a removable cap. In the embodiment shown, four securement pins 940 are used to secure the left and right sections 905, 907 together. The left and right members may also include a slot or aperture 950 in the top portion 908 which may be used for a variety of purposes, including but not limited to, insertion of a tool and handling of the left and right members during assembly.

It is noted that the terms "left" and "right" are used herein for purposes of explanation only, and any location or division of the sections or portions of the housing would be acceptable for purposes of the present invention.

Assembly of the left and right side portions 905, 907 of the spinal connection assembly 900 of FIGS. 57-61 may occur by arranging the left and right side members such that recesses 912 and 914, recesses 920 and 922, arcuate portions 932 and 934, and pin receptors 936 and 938 are aligned. The sidewalls 908, 910 of the left and right sections are placed in contact, and pins 940 are inserted into the combined pin receptors. The pin caps 948 may then be attached to secure the pins in place in the receptors.

Assembly of the first side portion 904 and second side portion 906 of the spinal connection assembly 900 then continues substantially identical to that described with respect to first side portion 104 and second side portion 106 of spinal connection assembly 100 shown and described with respect to FIGS. 1-14. Likewise, the method of use of the spinal connection assembly 900 shown in FIGS. 57-61 is substantially identical to spinal connection assembly 100 described with respect to FIGS. 15-17.

While the various assemblies of the device and assembly processes are described with a certain degree of specificity, alternative arrangements and orders of attachment of components would not depart from the overall scope of the present invention. Furthermore, while specific arrangements of spinal connection assemblies are described herein, it is noted that when multiple assemblies are interconnected or used by a physician, additional sizes of assemblies and alternative assemblies may be used in any combination. For example, different width assemblies may be chosen to accommodate for different spacings between respective posterior spinal connectors as well as for variations in locations of insertion of the connectors and for vertebral position.

Accordingly, the system and assemblies herein provide an assembly which is low profile, or not prominent. Generally, the assemblies are either side loading or bottom loading, and as a result are very low profile. In addition, a rod is positioned to the side of the screw in all embodiments, which allows for the low profile setting. From that home position, the assemblies further permit significant ranges of pivotal motion of the assembly relative to the head of the proximal spinal connector, including pivotal motion in at least one plane of at least approximately 180°, in a second plane of at least approximately 120°, and permitting pivotal motion about the axis of the screw head. The physician does not need to "persuade" the components of the assembly or the rod into place, because there is a significant degree of motion, permitted by the assemblies and additional sizes of side loading assemblies may be used. At most, all that may be required is the selection of a different width spinal connection assembly so as to avoid persuading the rod into the spinal connection assembly. It is not necessary to preload the assembly onto the posterior spinal connector. Moreover, it is not necessary to preload the screw that captures the rod. Therefore, it is not necessary to supply a significant amount of torque in order to allow the rod to be captured by adjacent or multiple assemblies. Thus, the physician does not torsionally affect the head of the pedicle screw.

In addition to advantages generally set forth herein, the spinal connection assembly 400 shown in FIGS. 25-31 has certain specific advantages. For example, by placing the connector element or rod 118 in the center portion 408 of the housing 402, the physician dissects less of the body during surgery as compared to a side-attached rod 118. In addition, in this embodiment, one rod 118 may be captured by two posterior spinal connectors 114, 418 or screws, increasing the strength of the anchor to vertebra and allowing the physician to have a centrally placed rod 118 which ultimately decreases the amount of trauma caused to the patient.

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g., attached, coupled, connected) are to be construed broadly and may include intermediate members between a connection of elements and relative movement between elements. As such, joinder references do not necessarily infer that two elements are directly connected and in fixed relation to each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to preferred embodiments, persons skilled in the art will recognize that changes may be made in form and detail without departing from the spirit and scope of the invention.

I claim:

1. A low-profile side-by-side spinal connection assembly for use with a posterior spinal connector having a head and a groove adjacent the head for providing a neck and a connector element to treat a spine of a mammalian body, the spinal connection assembly comprising a housing having first and second side portions and a top and a bottom, the first side portion being provided with a bottom-facing first opening adapted for receiving the posterior spinal connector and with first and second arcuate rails each having a length and extending towards the first opening, a capture mechanism carried by the first side portion for engaging the head of the posterior spinal connector and including first and second capture elements independent from each other disposed in spaced-apart positions within the first opening and moveable along the length of the respective first and second arcuate rails from an opened first position for receiving the head of the posterior spinal connector to a second position for capturing the head of the posterior spinal connector within the first opening, the second side portion being provided with a second opening, a securement mechanism carried by the second side portion for capturing the connector element within the second opening.

2. The spinal connection assembly of claim 1 wherein the connector element is a rod and the second opening is side-facing.

3. The spinal connection assembly of claim 1 wherein the connector element is a rod and the second opening is top-facing.

4. The spinal connection assembly of claim 1 wherein the connector element is a posterior spinal connector and the second opening is bottom-facing.

5. The spinal connection assembly of claim 4 for use with a rod, wherein the housing has a central portion provided with a top-facing opening for receiving the rod, further comprising an additional securement mechanism carried by the central portion for capturing the rod within the top-facing opening.

6. The spinal connection assembly of claim 1, wherein the connector element is a rod and the second opening is bottom-facing.

7. The spinal connection assembly of claim 1 for use with a rod, further comprising a side housing and cooperative attachment elements carried by the first side portion of the housing and the side housing for removably securing the side housing alongside the first side portion, the side housing being provided with a bottom-facing opening for receiving the rod, an additional securement mechanism carried by the side housing for capturing the rod within the bottom-facing opening of the side housing.

8. The spinal connection assembly of claim 7 for use with an additional rod, further comprising an additional side housing and cooperative attachment elements carried by the second side portion of the housing and the additional side housing for removably securing the additional side housing alongside the second side portion, the additional side housing being provided with a bottom-facing opening for receiving the additional rod, a further additional securement mechanism carried by the additional side housing for capturing the additional rod within the bottom-facing opening of the additional side housing.

9. The spinal connection assembly of claim 1 wherein each of the first and second capture elements includes a concave surface riding on the first and second arcuate rails for moving the first and second capture elements from the first position to the second position.

10. The spinal connection assembly of claim 9 wherein the capture mechanism further includes a capture screw for engaging the first and second capture elements and moving the capture elements from the first position to the second position.

11. The spinal connection assembly of claim 1 wherein the head of the posterior spinal connector is spherical in shape, each of the first and second capture elements having an inner spherical surface for engaging the spherical head of the posterior spinal connector.

12. The spinal connection assembly of claim 1 wherein the connector element is a rod and the securement mechanism includes first and second capture elements, the second side portion of the housing being provided with first and second arcuate rails and the first and second capture elements being disposed in spaced-apart positions within the second opening and moveable on the respective first and second arcuate rails from an opened first position for receiving the rod and a second position for capturing the rod.

13. The spinal connection assembly of claim 12 wherein the rod is cylindrical in shape, each of the first and second capture elements having an inner arcuate surface for engaging the rod.

14. The spinal connection assembly of claim 1 wherein the connector element is a screw.

15. The spinal connection assembly of claim 1, wherein the capture mechanism includes a limiting element for restricting axial travel of the posterior spinal connector within the housing.

16. The spinal connection assembly of claim 15 wherein the limiting element is a threaded connector that mates with a corresponding thread on the housing.

17. A spinal connection assembly for use with a connector element to treat a spine of a mammalian body, the spinal connection assembly comprising a housing and a securement mechanism, the housing having an opening adapted for receiving the connector element and the securement mechanism including first and second capture elements carried by the housing for capturing the connector element within the opening, the housing being provided with first and second arcuate rails each having a length and the first and second capture elements being independent from each other and disposed in spaced-apart positions within the opening and each having a concave arcuate surface riding along the length of the respective first and second arcuate rails for moving the first and second capture elements from an opened first position for receiving a portion of the connector element to a second position for capturing the portion of the connector element.

18. The spinal connection assembly of claim 17 wherein the connector element is a posterior spinal connector.

19. The spinal connection assembly of claim 18 wherein the portion of the posterior spinal connector is spherical in shape, each of the first and second capture elements having an inner spherical surface for engaging the spherical portion of the posterior spinal connector.

20. The spinal connection assembly of claim 17 wherein the connector element is a rod, each of the first and second capture elements having an inner arcuate surface for engaging the rod.

21. The spinal connection assembly of claim 17, wherein the securement mechanism includes a screw for moving the first and second capture elements.

22. A spinal connection assembly for use with a posterior spinal connector having a head and a groove adjacent the head for providing a neck to treat a spine of a mammalian body, the spinal connection assembly comprising a housing having a top and a bottom and being provided with a bottom-facing opening adapted for receiving the posterior spinal connector and with first and second arcuate rails each having a length and extending towards the opening, a capture mechanism carried by the housing for engaging the head of the posterior spinal connector and including first and second capture elements independent from each other disposed in spaced-apart positions within the opening and moveable along the length of the respective first and second arcuate rails from an opened first position for receiving the head of the posterior spinal connector to a second position for capturing the head of the posterior spinal connector within the opening.

23. The spinal connection assembly of claim 22 for use with a rod, further comprising a side housing and cooperative attachment elements carried by the first-named housing and the side housing for removably securing the side housing alongside the first-named housing, the side housing being provided with a bottom-facing opening for receiving the rod, an additional securement mechanism carried by the side housing for capturing the rod within the bottom-facing opening of the side housing.

24. The spinal connection assembly of claim 23 for use with an additional rod, further comprising an additional side housing and cooperative attachment elements carried by the first-named housing and the additional side housing for removably securing the additional side housing alongside the first-named housing opposite the first-named side housing, the additional side housing being provided with a bottom-facing opening for receiving the additional rod, a further additional securement mechanism carried by the additional side housing for capturing the additional rod within the bottom-facing opening of the additional side housing.

25. The spinal connection assembly of claim 22 for use with a rod, wherein the housing has a central portion provided with an top-facing opening for receiving the rod, further comprising a additional securement mechanism carried by the central portion for capturing the rod within the top-facing opening.

* * * * *